US012042242B2

United States Patent
Simi et al.

(10) Patent No.: US 12,042,242 B2
(45) Date of Patent: *Jul. 23, 2024

(54) ROBOTIC MICROSURGICAL ASSEMBLY

(71) Applicant: MEDICAL MICROINSTRUMENTS INC., Wilmington, DE (US)

(72) Inventors: Massimiliano Simi, Pisa (IT); Giuseppe Maria Prisco, Pisa (IT)

(73) Assignee: MEDICAL MICROINSTRUMENTS, INC., Wilmington, DE (US)

( * ) Notice: Subject to any disclaimer, the term of this patent is extended or adjusted under 35 U.S.C. 154(b) by 290 days.

This patent is subject to a terminal disclaimer.

(21) Appl. No.: 17/712,921

(22) Filed: Apr. 4, 2022

(65) Prior Publication Data

US 2022/0226061 A1 Jul. 21, 2022

Related U.S. Application Data

(63) Continuation of application No. 16/605,121, filed as application No. PCT/IB2018/052591 on Apr. 13, 2018, now Pat. No. 11,317,981.

(30) Foreign Application Priority Data

Apr. 14, 2017 (IT) .......................... 102017000041991

(51) Int. Cl.
*A61B 34/30* (2016.01)
*A61B 34/00* (2016.01)
(Continued)

(52) U.S. Cl.
CPC .............. *A61B 34/71* (2016.02); *A61B 34/37* (2016.02); *A61B 34/72* (2016.02); *B25J 9/106* (2013.01); *B25J 9/1615* (2013.01)

(58) Field of Classification Search
CPC ......... A61B 34/00; A61B 34/30; A61B 34/37; A61B 34/71; A61B 34/72; A61B 19/201;
(Continued)

(56) References Cited

U.S. PATENT DOCUMENTS 5,520,678 A * 5/1996 Heckele ................. A61B 34/71
606/1
5,710,870 A 1/1998 Ohm et al.
(Continued)

FOREIGN PATENT DOCUMENTS

| WO | 03/001986 A2 | 1/2003 |
| WO | 2010/009221 A2 | 1/2010 |
| WO | 2014/151952 A1 | 9/2014 |

OTHER PUBLICATIONS

International Search Report and Written Opinion of the International Searching Authority for International Patent Application No. PCT/IB2018/052591 mailed Jun. 4, 2018, 9 pages.

*Primary Examiner* — Vi X Nguyen
(74) *Attorney, Agent, or Firm* — Merchant & Gould P.C.

(57) ABSTRACT

A robotic surgical assembly includes a slave manipulator connected to a surgical instrument. A jointed subassembly includes at least first, second and third links. The first and second links are associated in a first joint providing a degree of freedom between the first link and the second link. The second and third links are associated in a second joint providing a degree of freedom between the second link and the third link. The surgical instrument includes a tendon for moving a degree of freedom; the tendon including a tendon distal portion secured to the third link. The first link and/or the second link includes a tendon contact surface on which the tendon slides remaining in contact with the tendon contact surface, defining one or more sliding paths on the
(Continued)

tendon contact surface. The sum of all sliding paths defines a total winding angle of at least 120°.

20 Claims, 22 Drawing Sheets

(51) Int. Cl.
*A61B 34/37* (2016.01)
*B25J 9/10* (2006.01)
*B25J 9/16* (2006.01)

(58) Field of Classification Search
CPC .... A61B 19/203; A61B 19/5244; B25J 9/106; B25J 9/1615
See application file for complete search history.

(56) References Cited

U.S. PATENT DOCUMENTS

| | | | |
|---|---|---|---|
| 5,808,665 A * | 9/1998 | Green | H04N 13/337 348/E13.016 |
| 6,676,684 B1 | 1/2004 | Morley et al. | |
| 6,840,938 B1 | 1/2005 | Morley et al. | |
| 7,155,316 B2 | 12/2006 | Sutherland et al. | |
| 2002/0120252 A1 | 8/2002 | Brock et al. | |
| 2002/0128661 A1 | 9/2002 | Brock et al. | |
| 2003/0135204 A1 | 7/2003 | Lee et al. | |
| 2015/0127045 A1 | 5/2015 | Prestel | |
| 2016/0051274 A1 | 2/2016 | Howell et al. | |
| 2017/0020615 A1 | 1/2017 | Koenig et al. | |

* cited by examiner

ROBOTIC MICROSURGICAL ASSEMBLY

This application is a Continuation of U.S. patent application Ser. No. 16/605,121 filed 14 Oct. 2019, which is a National Stage Application of PCT/162018/052591, filed 13 Apr. 2018, which claims the benefit of Serial No. 102017000041991, filed 14 Apr. 2017 in Italy, and which applications are incorporated herein by reference. To the extent appropriate, a claim of priority is made to each of the above-disclosed applications.

FIELD OF THE INVENTION

It is an object of the present invention a robotic surgical assembly.

In particular, the present invention relates to a robotic microsurgical assembly.

The present invention relates to a robotic microsurgical assembly of the type comprising a master tool manipulator and a surgical instrument.

The present invention also relates to a slave assembly as well as to a surgical instrument.

BACKGROUND

Robotic assemblies for surgery or microsurgery comprising multi-joint robotic arms terminating with surgical instruments are known in the field. For instance, document U.S. Pat. No. 7,155,316 discloses a robotic assembly for performing brain microsurgery under MRI (Magnetic Resonance Imaging) guidance comprising an MRI-based image acquisition system and two multi-joint arms, each with three rotary joints with vertical axes to avoid direct gravity loads (as shown for instance in FIG. 7 of said document U.S. Pat. No. 7,155,316), each connected to its respective end-effector endowed with an internal degree of freedom of motion for gripping.

It is also notable that the execution of the principal surgical primitives, such as tissue tensioning and anastomotic suturing, requires the ability to orient the surgical instrument tip in a large spatial cone of directions and to rotate the instrument around its longitudinal axis (roll), for example to guide the needle through the tissue with the tip of the needle holder instrument, in a similar manner as the human hand is jointed at the wrist and the elbow.

In order to simplify the miniaturization of a surgical instrument, the document WO-2010-009221 indicates the advantageous opportunity of reducing the number of actuation tendon terminations, associated to three degrees of freedom, from six to four, exploiting for actuation the torque that cables terminated on the yaw link apply on the pitch link (see FIG. 4-A of cited document) and requires to such purpose to pull and release selectively such cables, thanks to a kinematic mechanism comprising a number of gears. Moreover, the driving system described requires that each end of an actuation tendon is attached to a winch, that selectively winds the tendon inducing the pull. The presence of mechanical aspects such as said winch and said teeth, which are notoriously subject to lost motion, creates a difficult to drive a miniature articulation, because lost motion in the drive system is translated into an angular play at the joint, that increase as the articulating device gets smaller. Said driving system is also unsuited to keep a low preload on the actuation cables to further limit friction and wear.

Moreover, the solutions described for tendon termination comprise tortuous paths meant to trap the tendon in some sections. Such solutions require the use of cables that are sufficiently resistant to survive such trapping, such as steel cables or cables with larger diameter than otherwise required.

The proximal tension in a proximal portion of a tendon, such as a proximal portion extending proximally than an intermediate portion of the same tendon contacting a structural member or link, and the tension in the intermediate portion of said tendon contacting said structural member, whenever the tendon is pulling, are related by the capstan equation. With the tendon pulling and is defined as positive, the tension in said tendon after crossing said structural member or link is reduced in consequence of the sliding friction between the tendon and the structural member surface by a factor exponentially related to the product of the sliding friction coefficient between the tendon material and the structural member material, and the winding angle between the tendon and the structural member.

The capstan equation holds true also in its differential form that can be integrated along the total winding angle. So it holds true also for arbitrary shapes of the winding surface by using for winding angle the total change in tendon direction as a result of the contact with the structural member. A significant additional sliding friction not accounted for by the capstan equation is present in any sharp point contact between tendon and structural member, which should be thus avoided to minimize friction.

A number of wrist designs avoid altogether sliding friction on the tendons by making use of idle pulleys to route the tendon around the links, such as in WO-2014-151952 and U.S. Pat. No. 6,676,684. Their miniaturization is limited by the minimum feasible diameter of said idler pulleys.

Specifically, U.S. Pat. No. 6,676,684 shows actuation cables for actuating the links that wrap around an idle pulley (ref. 68) rotatably connected to said link. Therefore, the actuation cables avoid to slide onto the surfaces of the respective pulley, and rather the pulley rolls and the respective actuation cable is locally stationary with respect to the pulley surface. Moreover, the distal link comprises a rounded termination surface (ref. 58.6) around which the actuation cable is wound and firmly secured, in order to move the distal link.

U.S. Pat. No. 6,840,938 shows a three link wrist assembly and a yaw cable terminated on the third link that is routed with idle pulleys rotatably connected to the first link and second link and avoids slide onto the surfaces of the respective pulley, and rather the pulley rolls and the respective actuation cable is locally stationary with respect to the pulley surface. In other words, the yaw cable avoids contacting the first link and the second link on any sliding contact surfaces.

Other similar examples are shown in document US-2002-120252, wherein the actuation cable is fixed and wound around a pulley rotatably connected to a respective link to transmit motion to the link, and wherein termination of actuation cable is firmly secured to the link to be moved requiring the cable termination being stationary in respect to the link.

A number of wrist designs, in the effort to miniaturize the wrist subassembly, have the tendons contacting the structural bodies of the intermediate links and sliding on them to move the more distal links, such as described for example in US-2015-0127045, WO-03-001986, WO-2010-009221, US-2017-0020615 (FIG. 5B) and US-2016-0051274.

In all such cases, the designer is making sure he/she is limiting the sliding friction to a minimum possible by minimizing the tendon winding or wrap angle over the structural bodies of the links. Specifically in all such designs the tendons are routed along longitudinal holes or channels that pass through the structural body of the link. As a result, in the above design, when the wrist in its straight configuration, the tendons have practically zero winding angle on the structural bodies of the intermediate links, while when the wrist is bent at close to 90 degrees, the total winding angle of the tendons attached to the most distal link is close to 90 degrees.

The unavoidable requirements to fabricate holes or guiding channels in the structural body of the link and to feed in said holes or guiding channels said tendons represent a severe limitation to the miniaturization of such designs. It should be noted the essential role of such holes in constraining the tendon to stay close to the wrist subassembly. In fact, as the wrist subassembly takes its different configuration the tendon is constrained by different sides of the holes' surface which necessarily have to surround it completely. In other words, in all mentioned documents, the routing of tendons through holes is an essential feature of the design.

A number of wrist designs, such as described in US-2003-0135204, avoid the use of both idle pulleys and the use of holes or guiding channels in the structural body of the intermediate link. Said design employs cylindrical protrusions, on which the tendon slides, to guide the tendons to reach the most distal links. The winding angle of such tendons on the structural link one is still kept to a minimum, that can be estimated around 10 degrees from the drawings, when the wrist in in its straight configuration. In fact, such tendons are deflected by said cylindrical protrusions toward the center of the links. The design still make use of holes in the structural body of the base link to constrain the tendons to stay within the diameter of the link members when the distal links are bent (with a yaw movement). Fabrication of holes in the structural body of the base (first) link of the body remains a limiting factor for miniaturization.

Hence, there is a felt need to provide a tendon, or actuation cable, for a medical instrument with characteristics that render it suitable for extreme miniaturization without compromising its resistance or reliability in use.

Furthermore, there is a felt need to provide a tendon for a medical instrument that is suitable for gliding over at least one portion of said instrument with improved performance in terms of friction with respect to known solutions.

Furthermore, there is a felt need to provide a tendon for a slave surgical instrument exclusively meant to work under tensile load applied at its endpoints, without comprising solutions that might result in deflecting the path of the tendon, that would diminish its resistance.

It is felt the need to reduce the friction between a tendon and the surface on which said tendon slides and at the same time it is strongly felt the need to miniaturize surgical instruments for robotic surgery.

Solution

A scope of the invention described here is to overcome the limitations of known solutions as described above and to provide a solution to the needs mentioned with reference to the state of the art.

FIGURES

Further characteristics and advantages of the invention will appear from the description reported below of preferred embodiments, which are given as examples and are not meant to be limiting, which makes reference to the attached figures, in which.

DETAILED DESCRIPTION OF SOME PREFERRED EMBODIMENTS

Figure 1:
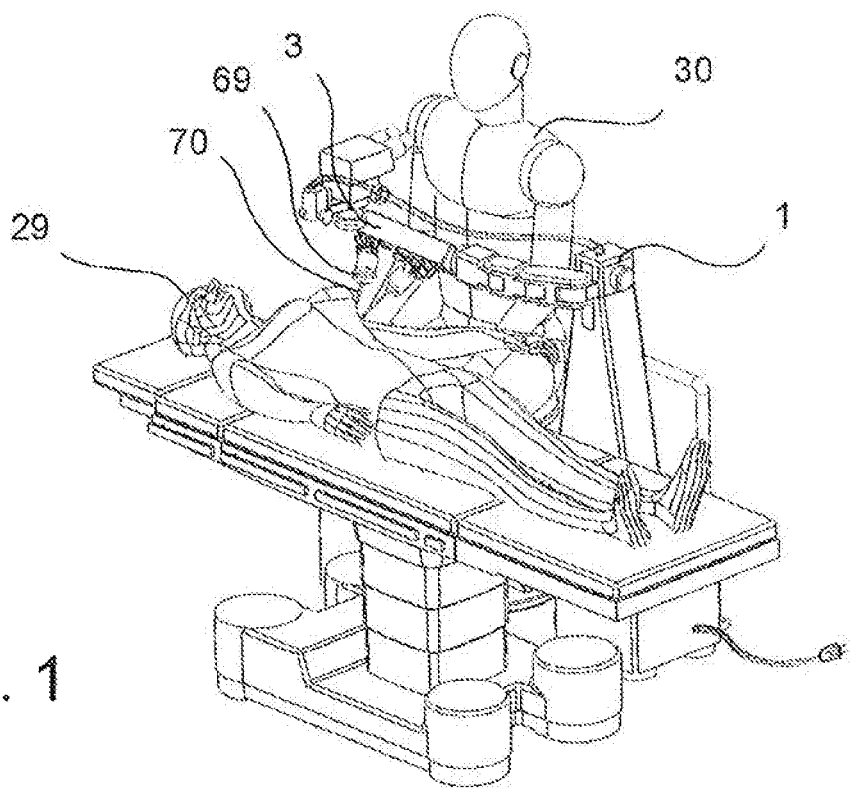
FIG. 1 is a perspective view of a robotic surgical assembly, according to an embodiment, wherein sketches depict a patient a surgeon.
Figure 2:
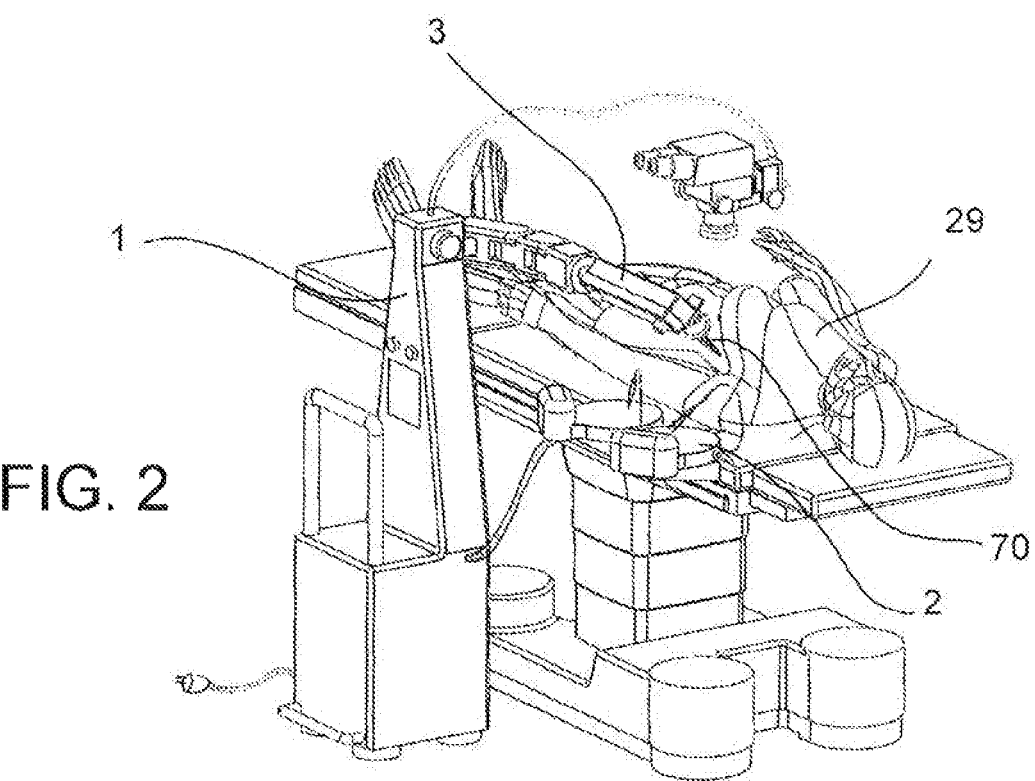
FIG. 2 is a perspective view of a robotic surgical assembly, according to an embodiment, wherein a sketch depicts a patient.
Figure 3A:
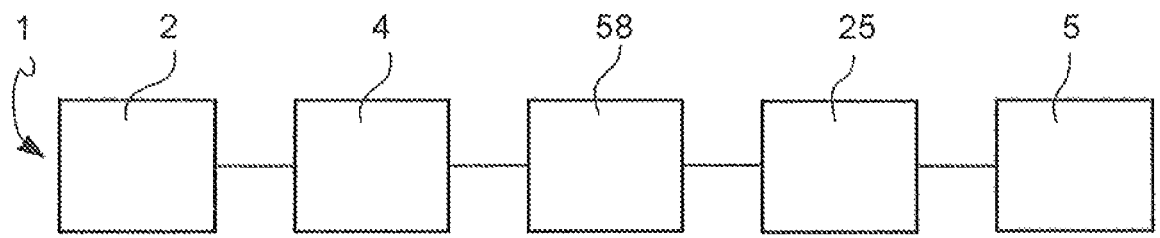
FIG. 3A is a block diagram of a robotic surgical assembly, according to an embodiment.
Figure 3B:
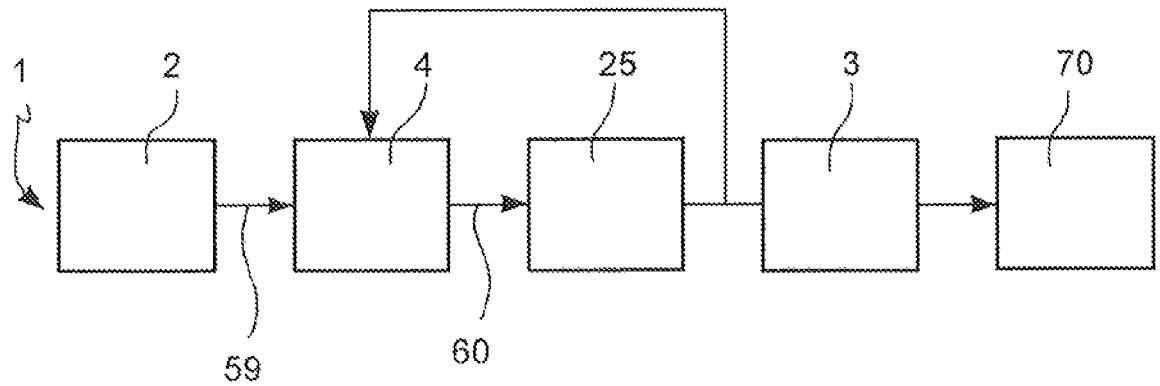
FIG. 3B is a block diagram of a robotic surgical assembly, according to an embodiment.
Figure 3C:
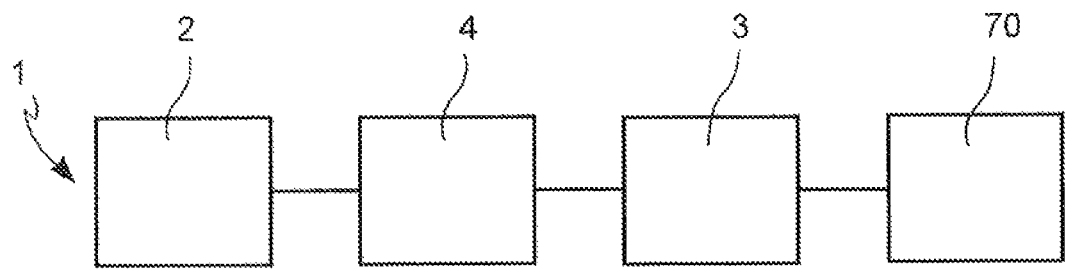
FIG. 3C is a block diagram of a robotic surgical assembly, according to an embodiment.
Figures 4, 5:
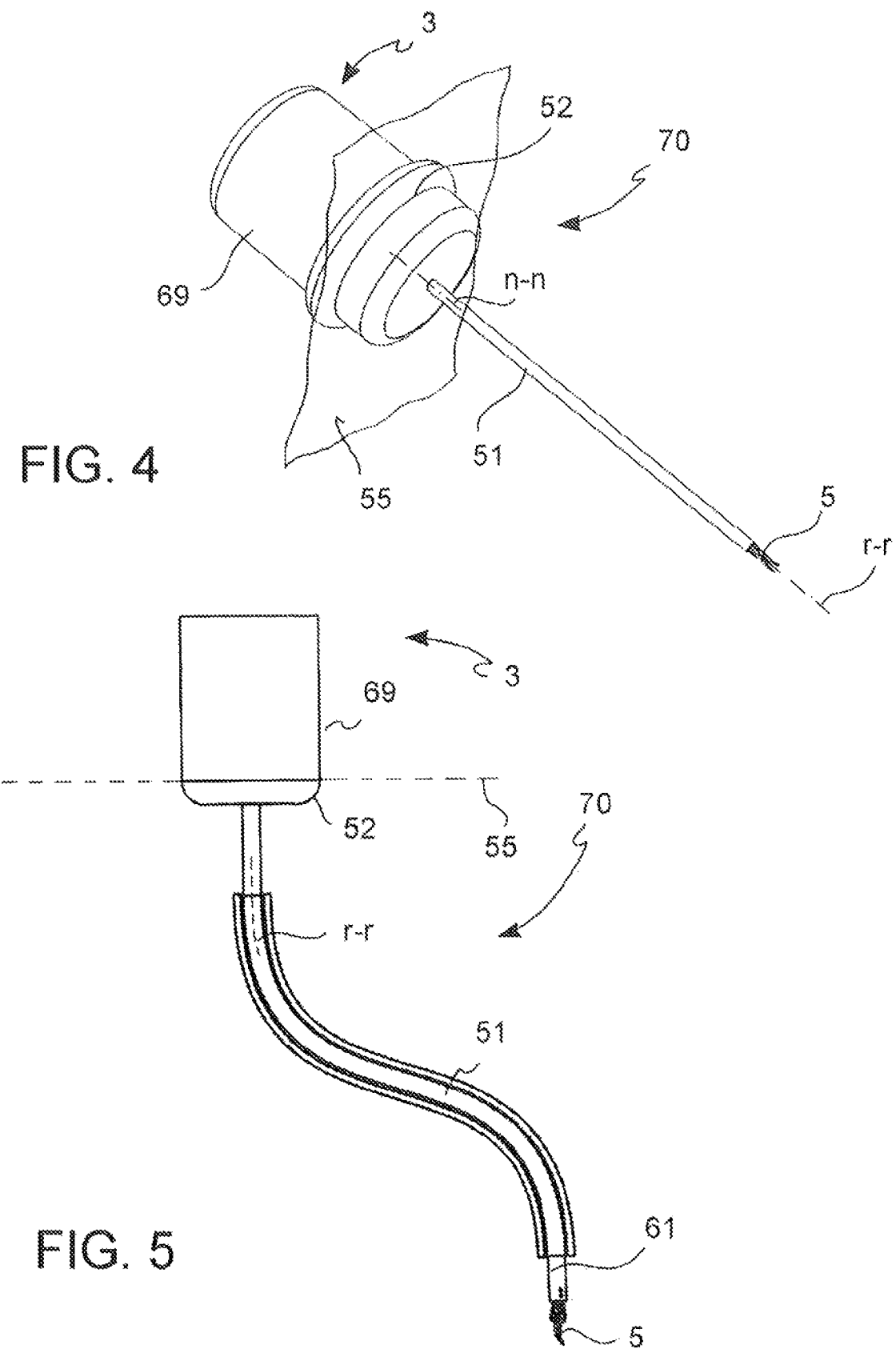
FIG. 4 is a perspective view of a portion of a slave manipulator connected to a surgical instrument, according to an embodiment.
FIG. 5 is a plan view of a portion of a slave manipulator connected to a surgical instrument, according to an embodiment.
Figure 6:
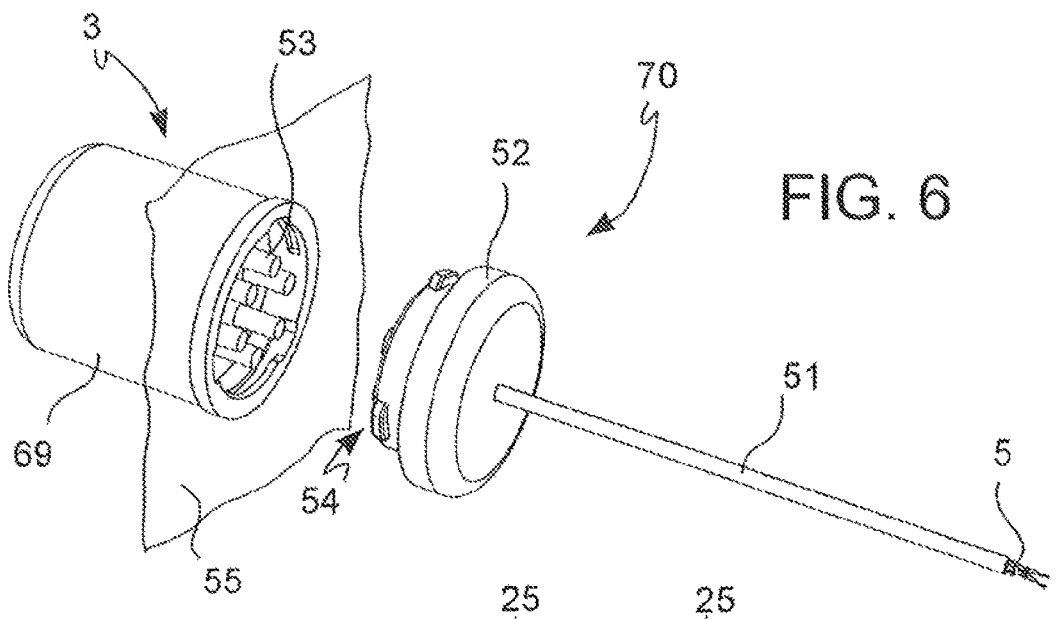
FIG. 6 is a perspective view of a portion of a slave manipulator disconnected from a surgical instrument, according to an embodiment.
Figure 7:
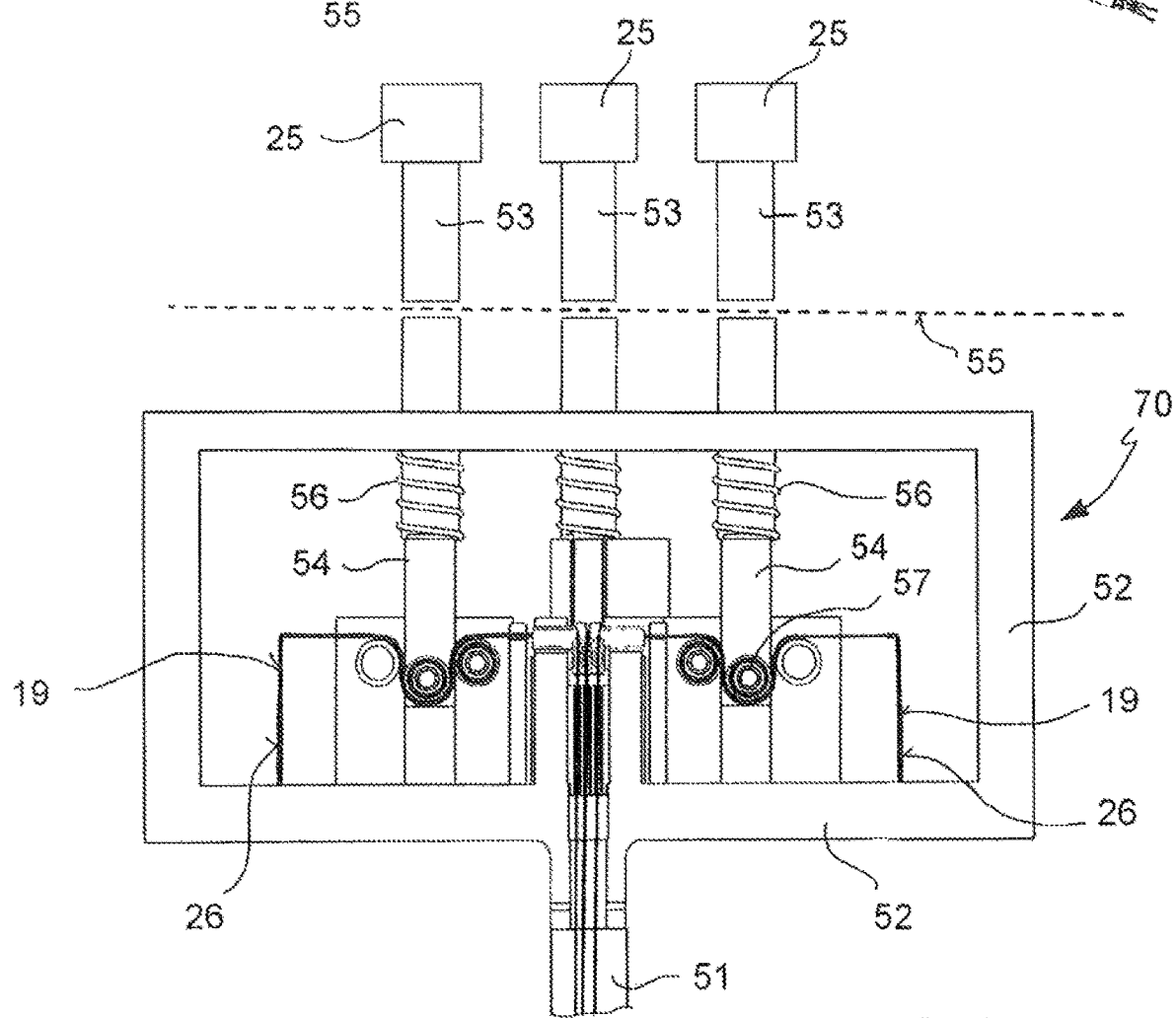
FIG. 7 is a sketch depicting a cross-section of a portion of a slave manipulator and a surgical instrument, according to an embodiment.
Figure 8:
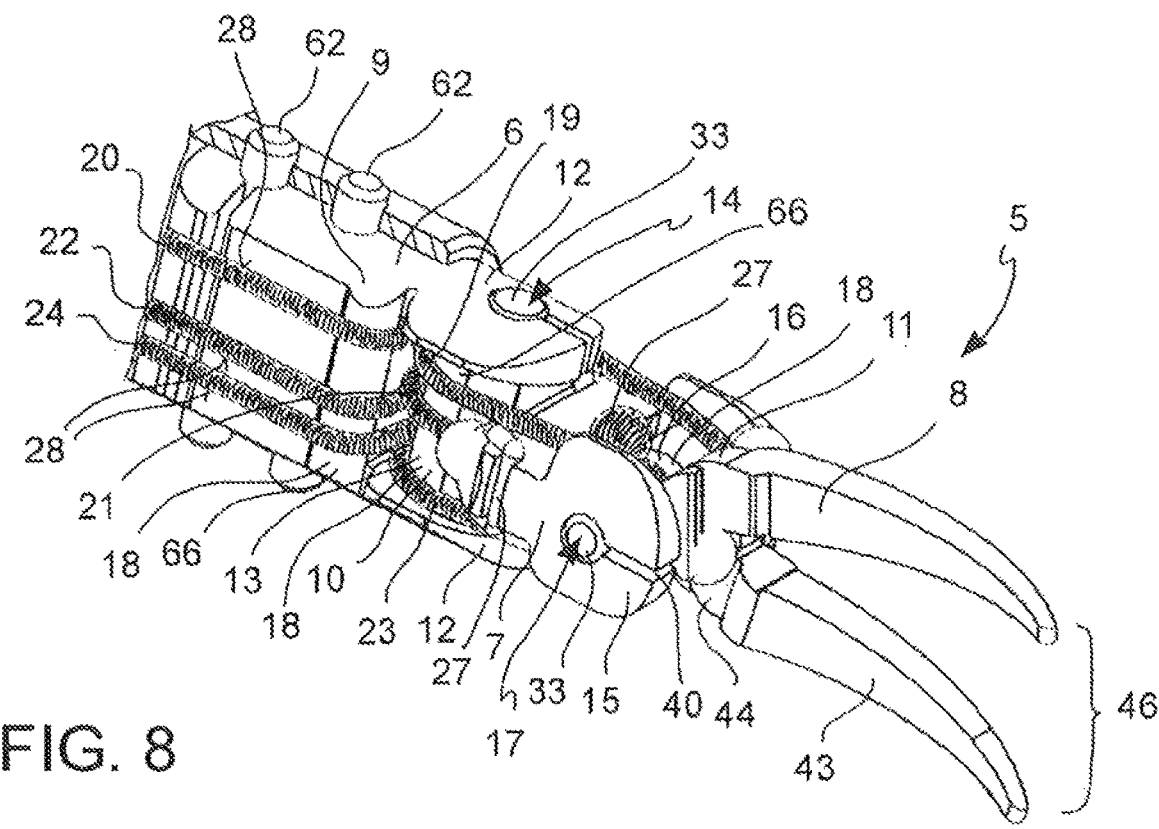
FIG. 8 is a perspective view of a jointed subassembly, according to an embodiment, wherein some parts are sectioned for sought of clarity.
Figure 9:
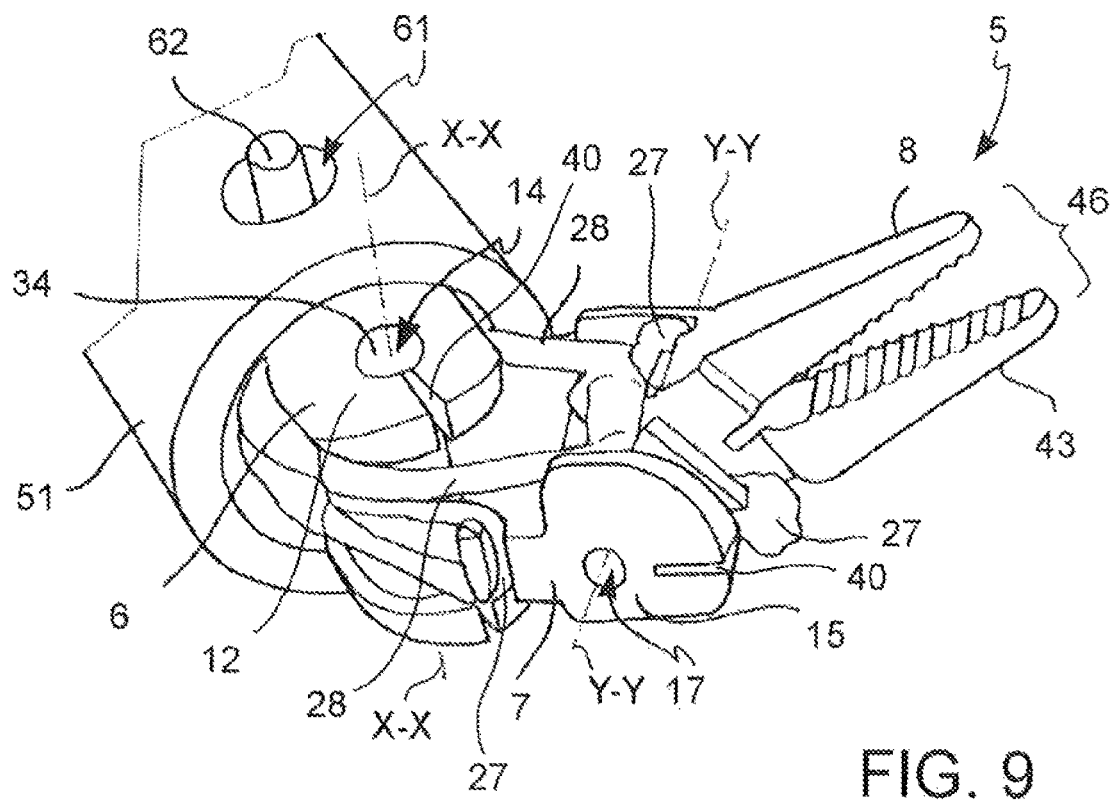
FIG. 9 is a perspective view of a jointed subassembly, according to an embodiment.
Figure 10:
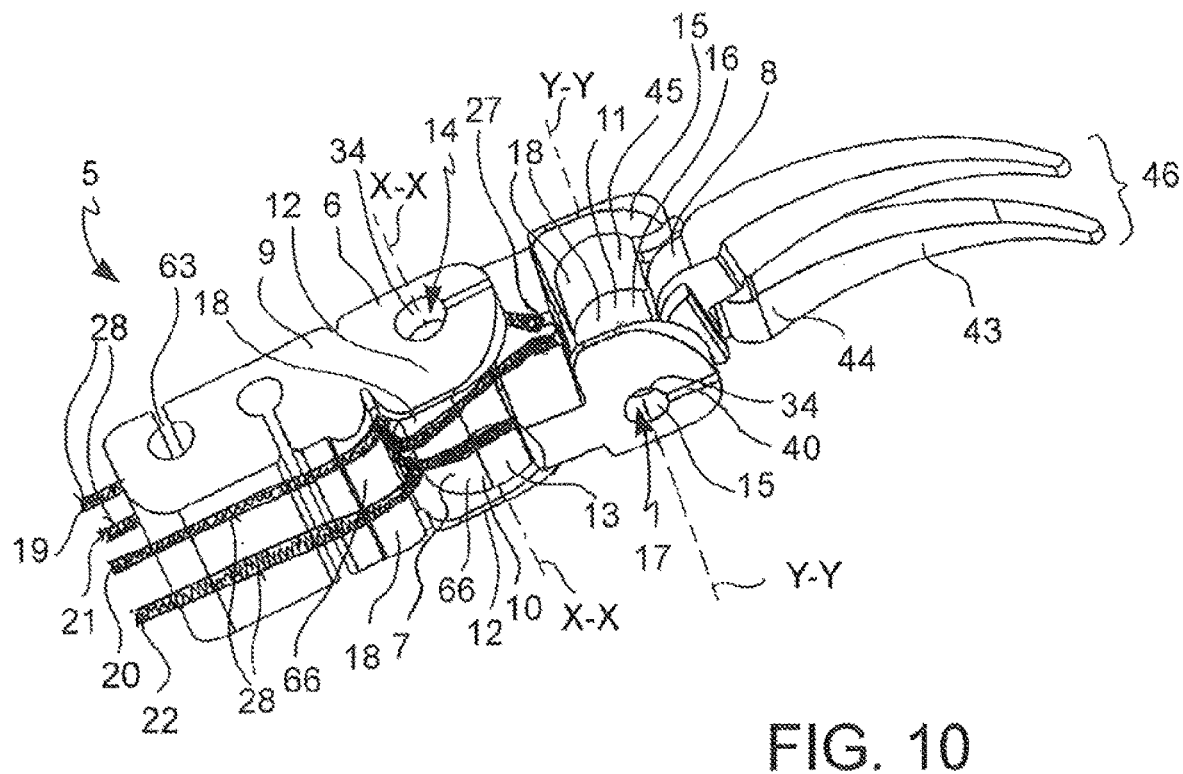
FIG. 10 is a perspective view of a jointed subassembly, according to an embodiment.
Figure 11:
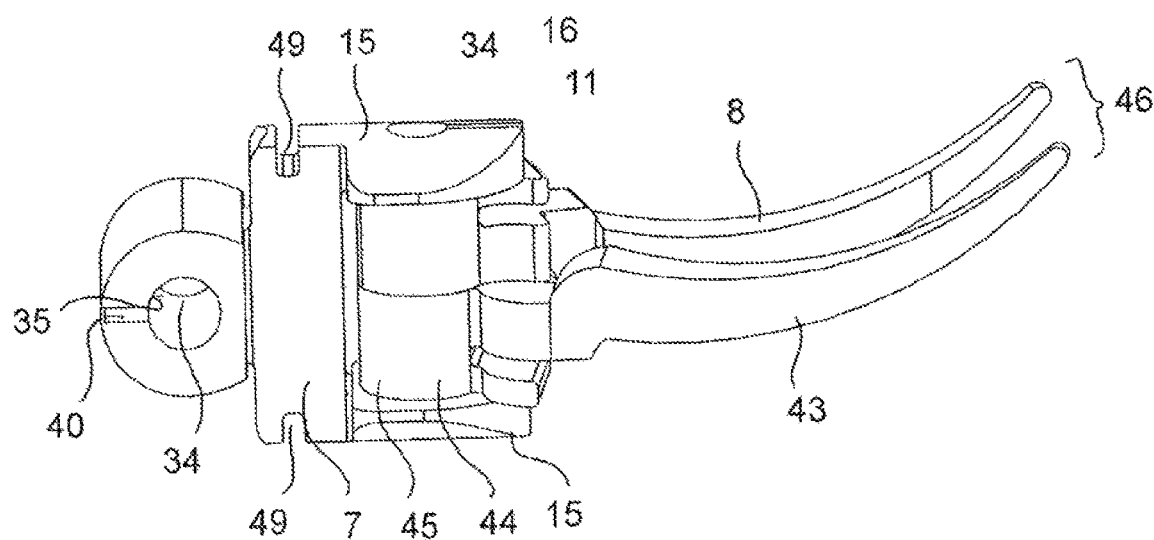
FIG. 11 is a perspective view of a portion of a jointed subassembly, according to an embodiment.
Figure 12:
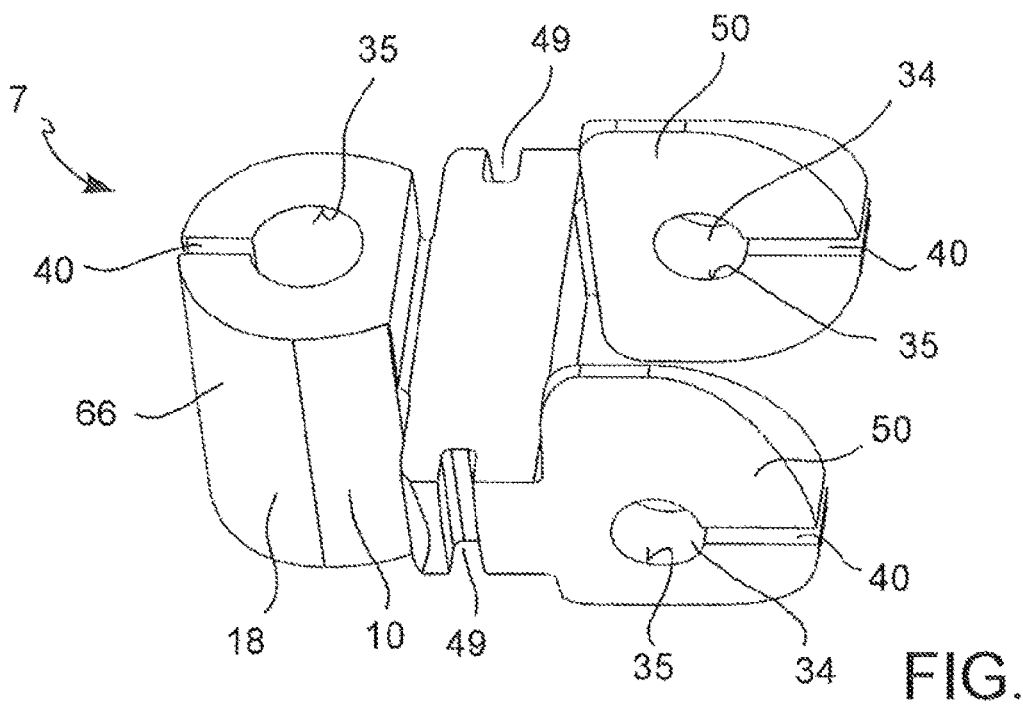
FIG. 12 is a perspective view of a link, according to an embodiment.
Figure 13A:
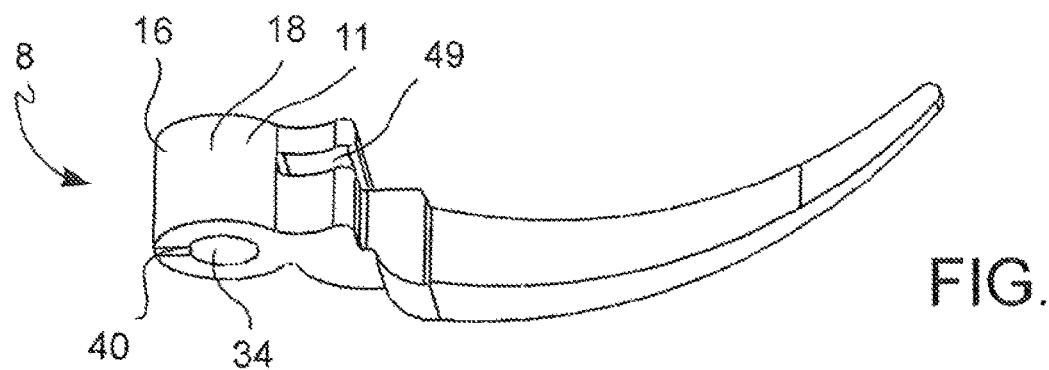
FIG. 13A is a perspective view of a link, according to an embodiment.
Figure 13B:
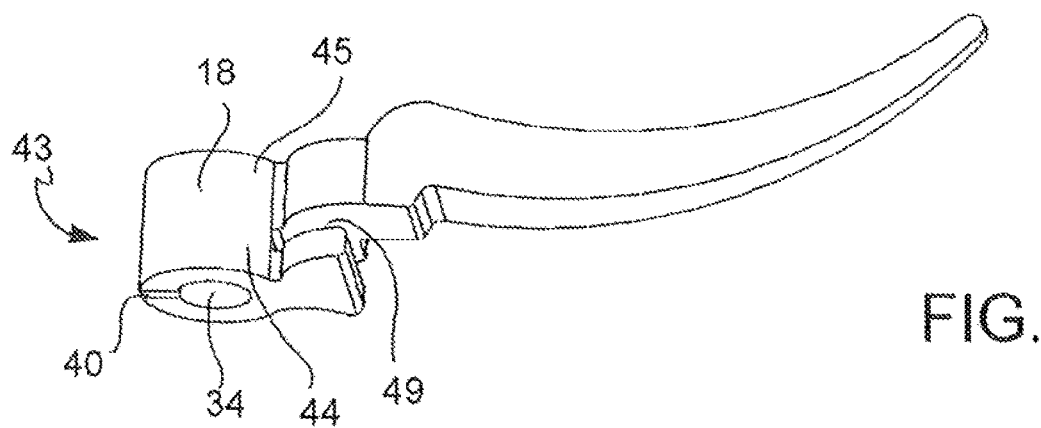
FIG. 13B is a perspective view of a link, according to an embodiment.
Figure 14:
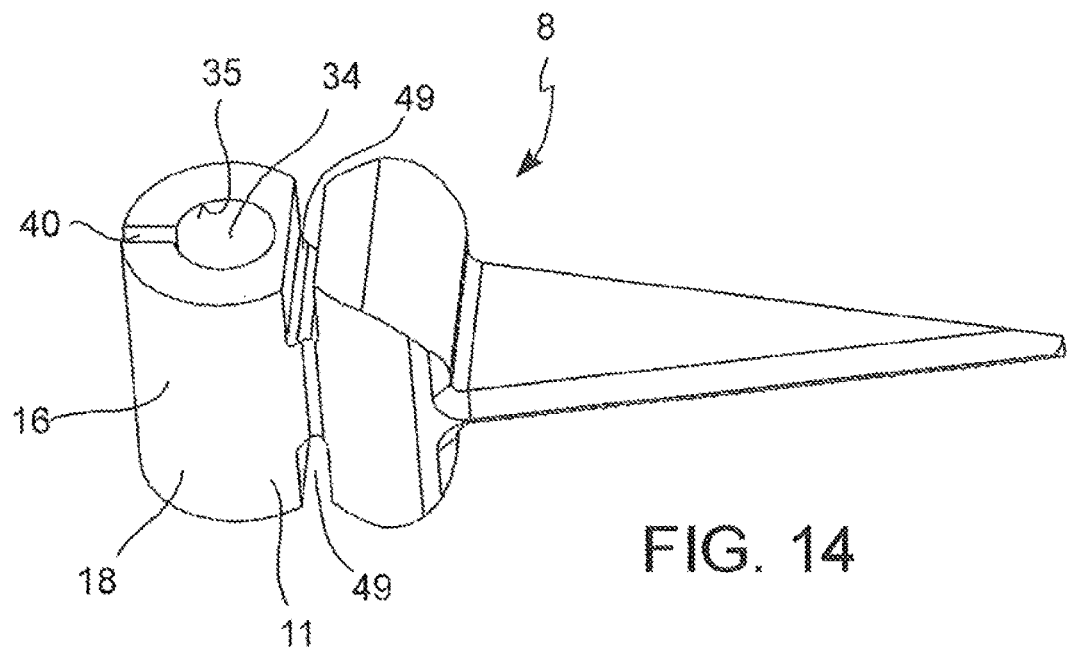
FIG. 14 is a perspective view of a link, according to an embodiment.
Figure 15:
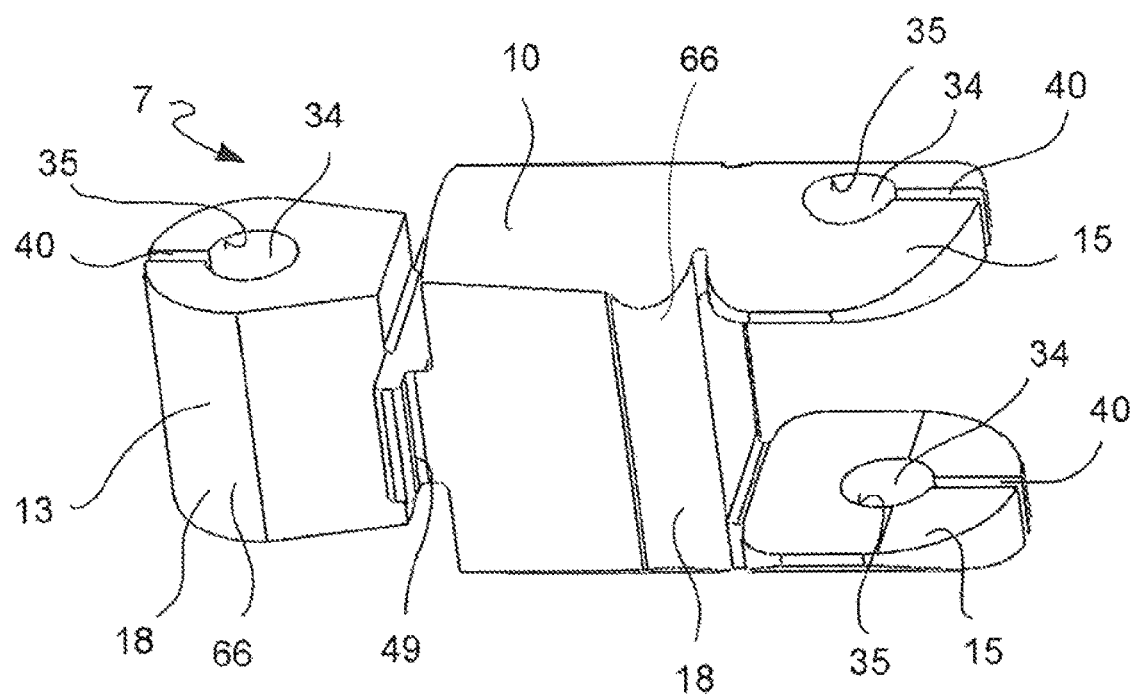
FIG. 15 is a perspective view of a link, according to an embodiment.
Figure 16:
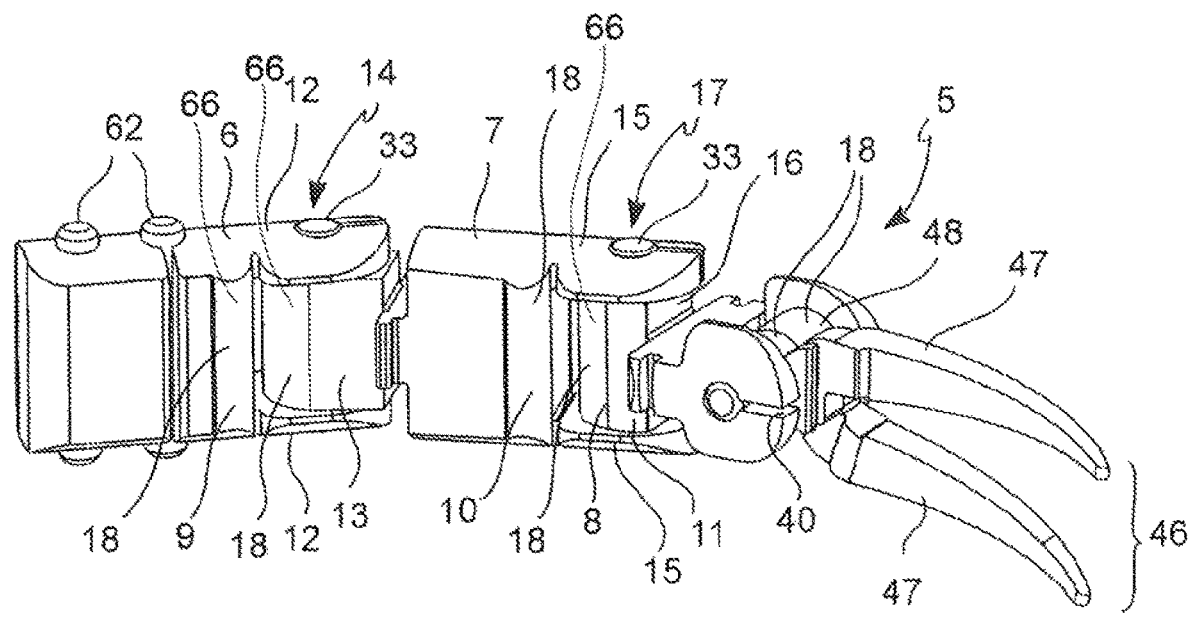
FIG. 16 is a perspective view of a jointed subassembly, according to an embodiment, wherein the tendons are not shown.
Figure 17:
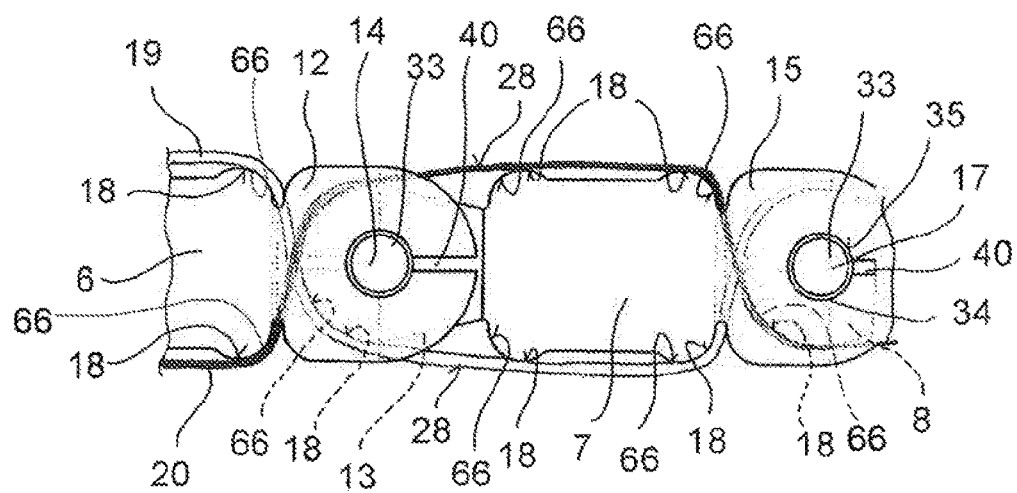
FIG. 17 is a sketch in plane view of a portion of a jointed subassembly, according to an embodiment, wherein tendons are shown.
Figure 18:
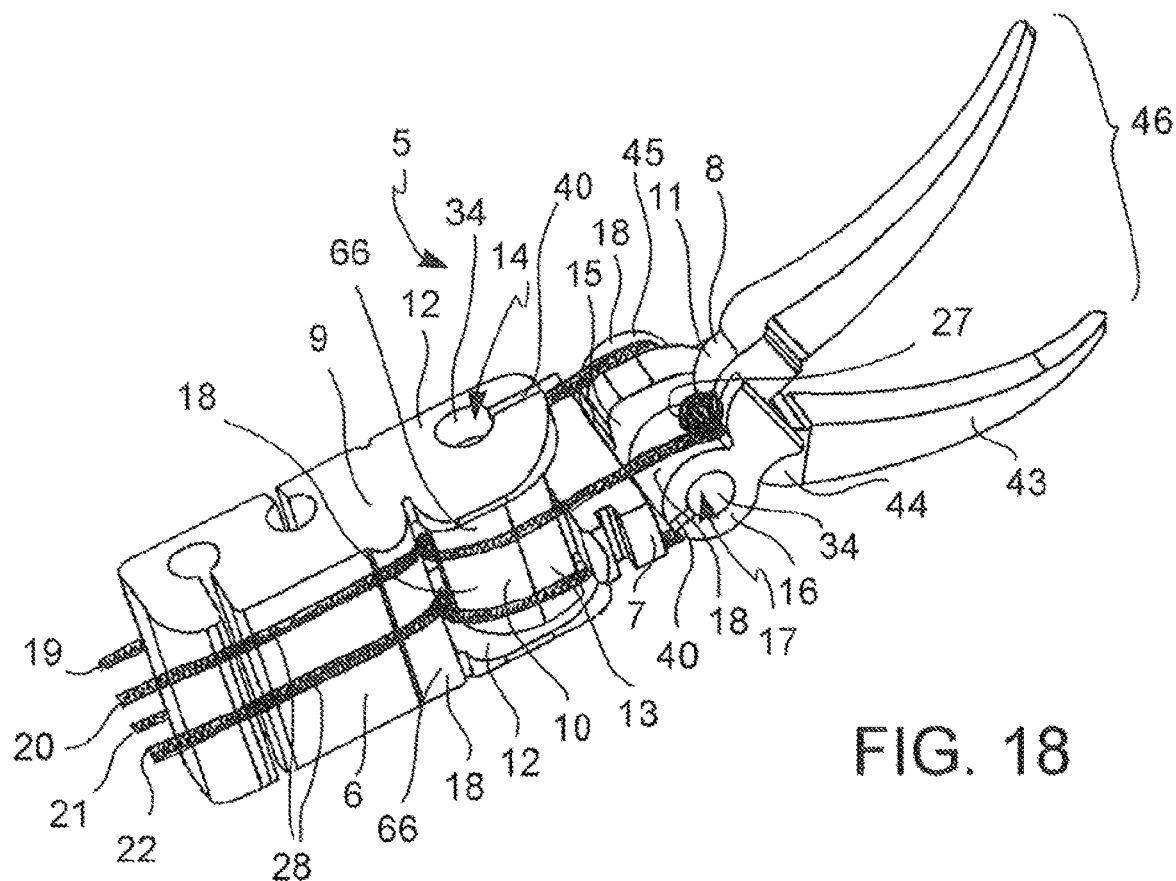
FIG. 18 is a perspective view of a jointed subassembly, according to an embodiment.

According to a general embodiment, a robotic surgical assembly 1 comprises a slave manipulator 3, a surgical instrument 70, connectable to said slave manipulator 3.

Said surgical instrument 70 comprises a jointed subassembly 5.

Said jointed subassembly 5 comprises at least a first link 6, a second link 7 and a third link 8;

According to an embodiment, a robotic microsurgery assembly 1 comprises at least one master tool 2, suitable to detect a manual command, at least one slave manipulator 3 and at least a surgical instrument 70, and at least one control unit 4 configured to receive at least a first command signal 59 comprising information about said manual command and to send a second command signal 60 to at least one actuator 25 in said slave manipulator 3 to control said surgical instrument 70.

According to an embodiment, said surgical instrument 70 is a slave surgical instrument 70. According to an embodiment, said surgical instrument 70 is a medical instrument 70.

Said surgical instrument 70 comprises a jointed subassembly 5 comprising at least a first link 6, a second link 7 and a third link 8.

Said first link 6 and said second link 7 are associated in a first joint 14 providing a degree of freedom between said first link 6 and said second link 7.

Said second link 7 and said third link 8 are associated in a second joint 17 providing a degree of freedom between said second link 7 and said third link 8.

Said surgical instrument 70 comprises at least a tendon 19 for moving a degree of freedom.

Said at least one tendon 19 is suitable for moving said third link 8 in respect of at least said second link 7. According to an embodiment, said surgical instrument 70 comprises at least a pair of tendons 19, 20 for moving a degree of freedom. According to an embodiment, said pair of tendons 19, 20 is suitable for moving said third link 8 in respect of at least said second link 7.

According to a preferred embodiment, said tendon 19 comprises a tendon proximal portion 26, suitable to be associated to at least an actuator 25, said actuator being preferably not placed in said jointed subassembly 5, a tendon distal portion 27, secured to said third link 8, and a tendon intermediate portion 28, extending between said tendon proximal portion 26 and said tendon distal portion 27. For example, said at least one actuator 25 is located in an actuator compartment 69 portion of said slave manipulator 3 placed upstream with respect of the jointed subassembly 5.

At least one between said first link 6 and said second link 7 comprises at least one tendon contact surface 18 on which said tendon 19, and preferably said tendon intermediate portion 28, slides remaining in contact with said at least one tendon contact surface 18, defining one or more sliding paths 65 on said at least one tendon contact surface 18. In this way said at least one tendon contact surface 18 is a tendon sliding surface 66.

According to a preferred embodiment, said at least one tendon sliding surface 66 of either said first link 6 and said second link 7 is a smooth surface having a surface profile without sharp edges.

According to a preferred embodiment, said at least one tendon contact surface 18 of either said first link 6 and said second link 7 is a smooth surface having a surface profile without sharp edges.

According to a preferred embodiment, said at least one tendon contact surface 18 of either said first link 6 and said second link 7 is a tendon sliding surface 66, on which said tendon 19 slides having local relative motion with said at least one tendon sliding surface 66, while remaining in contact with said at least one tendon contact surface 18. In other words, according to an embodiment, said at least one tendon contact surface 18 on which said tendon intermediate portion slides, is a tendon sliding surface 66. In other words, according to one embodiment, a local relative sliding motion takes place between said tendon and said at least one tendon contact surface 18 when the jointed device configuration changes from a first configuration to a second configuration. In other words, according to one embodiment, a local sliding friction force is generated between said tendon and said at least one tendon contact surface 18 during motion of the jointed device.

According to one embodiment, the term "slides" and the term "sliding" both refer to contact with local relative sliding motion. According to one embodiment, the term "slides" and the term "sliding" both refer to contact that generates local sliding friction force. According to one embodiment, the term "slides" and the term "sliding" both avoid referring to contact without local relative sliding motion, such as contacts between a tendon and an idle pulley and such as contact between a tendon and a surface on which said tendon is terminated and is winded.

According to a preferred embodiment, said at least one tendon contact surface 18 of either said first link 6 and said second link 7 is a tendon sliding surface 66, on which said tendon 19 slides remaining in contact with said at least one tendon sliding surface 66. In other words, according to an embodiment, said at least one tendon contact surface 18 on which said tendon intermediate portion slides, is a tendon sliding surface 66. According to an embodiment, said third link 8 comprises at least one tendon contact surface 18 and said tendon touches said tendon contact surface 18 of said third link 8 avoiding to slide thereon. According to an embodiment, said tendon distal portion 27 is unsuitable for sliding on a tendon contact surface 18.

According to an embodiment, said sliding path 65 has substantially a prevailing longitudinal extension. According to an embodiment, said sliding path 65 is the imprint that the tendon 19 defines on said tendon sliding surfaces 66. According to a preferred embodiment, each of said one or more sliding paths 65 is a continuous path. According to an embodiment, said tendon 19 and said tendon sliding surface 66 exchange local frictional forces as a result of the local relative motion. According to an embodiment, said tendon slides on said at least one tendon contact surface 18 along, or parallel to, the direction of its longitudinal development T-T, or tendon longitudinal path T-T. According to an embodiment, said tendon avoid to slide on said at least one tendon contact surface 18 in a direction transversal to the tendon longitudinal path T-T. According to an embodiment, said tendon longitudinal path T-T is stationary over the time. According to an embodiment, said one or more sliding paths 65 are coincident or parallel to a portion of said tendon longitudinal path T-T.

According to an embodiment, said sliding path 65 comprises and proximal or initial sliding path end, characterized by an initial tendon path direction immediately before said initial sliding path end, and a distal or final sliding path end, characterized by a final tendon path direction immediately after said final sliding path end. According to an embodiment, said tendon intermediate portion 28 is deflected by said at least one of first link 6 and second link 7. According to an embodiment, said tendon intermediate portion 28 is deflected by said at least one of first link 6 and second link 7 from an initial tendon path direction to final tendon path direction. According to an embodiment, said tendon intermediate portion is deflected by said at least one of first link 6 and second link 7 by a tendon deflection angle. According to an embodiment, said tendon deflection angle is measured as the angle between said initial tendon path direction and said final tendon path direction. According to an embodiment, said tendon intermediate portion is deflected by said at least one of first link 6 and second link 7 by one or more tendon deflection angles. According to an embodiment, a total deflection angle is the sum of all said tendon deflection angles. According to an embodiment, in at least one configuration of said jointed subassembly 5, said total deflection angle $\alpha+\beta$ is equal to or greater than 120 degrees. According to an embodiment, a straight configuration of said jointed subassembly has said link 2 and 3 at the center of their joint range of motion. According to an embodiment, in said straight configuration of said jointed subassembly 5, said total deflection angle $\alpha+\beta$ is equal to or greater than 90 degrees.

According to a preferred embodiment, said total tendon deflection angle $\alpha+\beta$ is said total winding angle $\alpha+\beta$.

According to a preferred embodiment, said at least one tendon longitudinal path T-T is tangent to said at least one tendon sliding surface 66 of either said first link 6 and said second link 7 at said initial sliding path end. According to a preferred embodiment, said at least one tendon longitudinal path T-T is tangent to said at least one tendon sliding surface 66 of either said first link 6 and said second link 7 at said final sliding path end. According to a preferred embodiment, for every jointed assembly configuration, said at least one tendon longitudinal path T-T is a smooth continuous curve, without angles.

Advantageously, the sum of all the sliding paths 65 of all the tendon sliding surfaces 66 of said first link 6 and of said second link 7 defines a total winding angle $\alpha+\beta$.

According to a preferred embodiment, the sum of all the sliding paths 65 of all the tendon sliding surfaces 66 defines a total winding angle $\alpha+\beta$.

According to an embodiment, the sum of all the sliding paths 65 of all the tendon sliding surfaces 66 sweeps a total winding angle $\alpha+\beta$. According to an embodiment, the sum of all the sliding paths 65 of all the tendon sliding surfaces 66 is covered by a total winding angle $\alpha+\beta$.

According to an embodiment, a single sliding path of a tendon sliding surface 66 of one link between said first link 7 and said second link 8 defines a local winding angle $\alpha$ or $\beta$. According to an embodiment, the sum of all said local winding angles defines said total winding angle $\alpha+\beta$. According to an embodiment, a single sliding path 65 of a tendon sliding surface 66 of one link between said first link 7 and said second link 8 defines a first local winding angle $\alpha$. According to an embodiment, a single sliding path 65 of a tendon contact surface 18 of one link between said first link 7 and said second link 8 defines a second local winding angle $\beta$.

According to an embodiment, said winding angle and said total winding angle refers to contact that generates local sliding friction force between said tendon and said at least one link between said first link 7 and said second link 8. According to an embodiment, said winding angle and total winding angle refers to contact that generates local sliding friction force between said tendon and said at least one link between said first link 7 and said second link 8 that increases with said winding angle.

Advantageously, in at least one configuration of said jointed subassembly 5, said total winding angle $\alpha+\beta$ is equal to or greater than 120 degrees.

According to an embodiment, said total winding angle ($\alpha+\beta$) is equal to or greater than 90 degrees when said jointed subassembly 5 is in its straight configuration.

According to an embodiment, the term "configuration" indicates a spatial geometrical positioning of said jointed subassembly 5. According to an embodiment, the term "configuration" indicates the relative spatial positioning and orientation of the links 6, 7, 8 forming said jointed subassembly 5. According to an embodiment, the term "straight configuration" indicates that the kinematic chain formed by said jointed subassembly 5 is substantially unfolded and/or extended to its maximum elongation.

According to an embodiment, one between said first link 6 and said second link 7 comprises at least two tendon contact surfaces 18, on which said tendon 19, and preferably said tendon intermediate portion 28, slides remaining in contact with both said at least two tendon sliding surface 66, defining said one or more sliding paths 65 on said at least two tendon contact surfaces 18.

According to an embodiment, said first link 7 comprises at least one tendon contact surfaces 18, on which said tendon 19, and preferably said tendon intermediate portion 28, slides remaining in contact with said at least one tendon sliding surface 66, defining said one or more sliding paths 65 on said at least one tendon sliding surface 66, and said second link 8 comprises at least one further tendon contact surfaces 18, on which said tendon 19, and preferably said tendon intermediate portion 28, slides remaining in contact with said at least one further tendon sliding surface 66, defining said one or more sliding paths 65 on said at least one further tendon sliding surface 66.

According to an embodiment, said jointed subassembly 5 comprises at least two tendon contact surfaces 18 being said tendon sliding surfaces 66, on which said tendon 19, and preferably said tendon intermediate portion 28, slides remaining in contact with both said at least two tendon sliding surfaces 66, defining said one or more sliding paths 65 on said at least two tendon sliding surfaces 66.

According to an embodiment, said third link 8 comprises at least a tendon contact surface 18 which is unsuitable for said tendon 19, and preferably for said tendon distal portion 27, to slide thereon.

According to an embodiment, each of said local winding angles is defined as the angle subtended to said tendon sliding surface 66. According to an embodiment, said total winding angle $\alpha+\beta$ is defined as the sum of all said local winding angles.

According to an embodiment, each of said local winding angles is defined as the angle formed by the two orthogonal lines to said tendons directed along said tendon longitudinal path T-T and defined in portions of said tendons that delimits the contact path 65 on said tendon sliding surface 66.

According to an embodiment, each of said local winding angles is defined as the angle formed by the two tendon longitudinal path T-T directions and defined in portions of said tendons that delimits the contact path 65 on said tendon sliding surface 66.

According to an embodiment, said at least one tendon sliding surface 66 comprises a proximal contact surface border 67 and a distal contact surface border 68 which delimit said tendon contact surface 18 along said tendon longitudinal path T-T, wherein said proximal contact surface border 67 is located proximally in respect of said distal contact surface border 68. According to an embodiment, each of said local winding angles is defined as the angle formed by the orthogonal lines to said tendon longitudinal path T-T evaluated immediately before said proximal contact surface border 67 and said tendon longitudinal path T-T evaluated immediately after said distal contact surface border 68.

According to an embodiment, said at least one tendon contact surface 18 comprises a proximal contact surface border 67 and a distal contact surface border 68 which delimit said tendon sliding surface 66 along said tendon longitudinal path T-T, wherein said proximal contact surface border 67 is located proximally in respect of said distal contact surface border 68. According to an embodiment, each of said local winding angles is defined as the angle formed by said tendon longitudinal path T-T direction evaluated immediately before said proximal contact surface border 67 and said tendon longitudinal path T-T direction evaluated immediately after said distal contact surface border 68.

According to an embodiment, each local winding angle $\alpha$ or $\beta$ is defined on a surface on which said tendon slides while remaining in contact, even if said surface is discontinuous or has sharp points.

According to an embodiment, each local winding angle $\alpha$ or $\beta$ is measured with reference to the center of the osculator circle to a single tendon sliding surface 66.

According to an embodiment, all contact points of a single tendon sliding surface 18 of a link embraces a portion of said link in such way to define a local winding angle $\alpha$ or $\beta$.

According to an embodiment, said total winding angle $\alpha+\beta$ is comprised between 60 degrees and 300 degrees.

According to an embodiment, said total winding angle $\alpha+\beta$ is comprised between 90 degrees and 270 degrees.

According to an embodiment, each link 6, 7, 8 has a link encumber. According to an embodiment, said at least one tendon contact surface 18 delimits at least partially said link encumber of a link.

According to an embodiment, said tendon contact surface 18 is cylindrical. According to an embodiment, said tendon sliding surface 66 is a portion of a cylindrical surface.

According to a preferred embodiment, said tendon is made of polymeric material.

According to an embodiment, said tendon is made of a material chosen in the group consisting of: polyethylene, ultra-high molecular weight polyethylene or UHMWPE, Kevlar®, Vectran®, Zylon®, polybenzobisoxazole, carbon fibers and combinations thereof.

According to a preferred embodiment, said tendon intermediate portion 28 is made of polymeric material. In this way, it is possible to provide said tendon intermediate portion 28 with less friction, less wear over the life time, thus less upkeep, and it is possible to realize said tendon intermediate portion 28 having inferior diameter in respect of tendons in other materials.

According to an embodiment, said tendon intermediate portion 28 is made of a material chosen in the group consisting of: polyethylene, ultra-high molecular weight polyethylene or UHMWPE, Kevlar®, Vectran®, Zylon®, polybenzobisoxazole, carbon fibers and combinations thereof.

According to an embodiment, said at least one tendon contact surface 18 is made of a material chosen in the group consisting of: steel, ceramic, carbide, titanium, liquid metal, and combinations thereof.

According to an embodiment, said at least one tendon sliding surface 66 is made of a material chosen in the group consisting of: steel, ceramic, carbide, titanium, liquid metal, and combinations thereof.

According to a preferred embodiment, said tendon intermediate portion 28 is made of ultra-high molecular weight polyethylene and said at least one tendon sliding surface 66 is made of steel alloy. According to a preferred embodiment, said tendon is made of ultra-high molecular weight polyethylene and said at least one tendon sliding surface 66 is made of steel. In this way, it is possible to obtain a friction coefficient in the range 0.04 to 0.08. In this way, stiction of the tendon intermediate portion 28 is avoided.

According to an embodiment, the dry sliding friction between said tendon sliding surface 66 and said tendon intermediate portion 28 has a friction coefficient equal to or lower than 0.1. For example, the dry sliding friction of such a tendon intermediate portion 28 over such tendon sliding surface 66 is more than five times less that the dry sliding friction defined by a metal tendon intermediate portion sliding over a metal tendon sliding surface that will result in the latter case to have a friction coefficient equal to substantially 0.5.

According to a preferred embodiment, said friction coefficient is lower than 0.1.

According to an embodiment, said total winding angle is substantially equal to 360 degrees. It is worth noting that the total friction in a tendon sliding over a tendon sliding surface over a winding angle is proportional to the tendon tension multiplied by the exponential of the product between the friction coefficient and the winding angle. Thus, a reduction of the friction coefficient allows to employ a proportionally larger winding angle. Being able to employ a larger winding cable opens up the possibility to route the tendons over the link structural bodies, avoiding the use of tendon guiding elements difficult to miniaturize.

According to an embodiment, the encumber of said links 6, 7 8 has a maximum extension, in a direction transversal to the longitudinal extension of said jointed subassembly 5 equal to or lower than 8 millimeters, and preferably equal to or lower than 5 millimeters, and preferably measuring in range from 2 millimeters to 5 millimeters.

According to an embodiment, said jointed subassembly 5 fits in its entirety in a cylindrical volume having a diameter measuring in range from 2 millimeters to 5 millimeters.

According to a preferred embodiment, said tendon intermediate portion 28 has a diameter equal to or lower than 0.5 millimeters and preferably comprised between 0.005 millimeters and 0.5 millimeters.

According to an embodiment, said tendon has a substantially circular cross section. According to an embodiment, the diameter of said tendon is variable in different portions of said tendon. According to an embodiment, the mechanical properties of said tendon are variable in different portions of said tendon. According to an embodiment, said tendon is obtained by joining portions of tendons with different characteristics. According to an embodiment, said tendon is connected to a stiffening rod element in the straight section running inside the shaft hollow core. According to an embodiment, said tendon is obtained by joining portions of tendons with different characteristics.

According to an embodiment, said at least one tendon sliding surface 66 is made of a material chosen in the group consisting of: steel, ceramic, titanium, carbide, and combinations thereof. According to an embodiment, said at least one of said structural body link is fabricated by micro injection molding. According to an embodiment, said at least one of said structural body link is fabricated by micro injection molding of liquid metal for best final dimensional tolerance, as known in the state of the art, parts below 5 mm in maximum dimension without through holes. According to an embodiment, said at least one of said structural body link is fabricated by micro injection molding of liquid metal for best mechanical performance esp. resilience and lack of fragile points.

According to a preferred embodiment, said tendon intermediate portion 28 is made of ultra-high molecular weight polyethylene and said at least one tendon sliding surface 66 is made of steel. According to a preferred embodiment, said tendon is made of ultra-high molecular weight polyethylene and said at least one tendon sliding surface 66 is made of steel. In this way, it is possible to obtain a friction coefficient equal to or lower than 0.04. In this way, striction of the tendon intermediate portion 28 is avoided.

According to an embodiment, the dry sliding friction between said tendon sliding surface 66 and said tendon intermediate portion 28 has a friction coefficient equal to or lower than 0.1. According to an embodiment, the dry sliding friction between said tendon sliding surface 66 and said tendon 19 has a friction coefficient equal to or lower than 0.1.

According to a preferred embodiment, said friction coefficient is lower than 0.1.

According to an embodiment, said total winding angle is substantially equal to 360 degrees. For example, the dry sliding friction of such a tendon intermediate portion 28 over such tendon contact surface 18 is less that the dry sliding friction defined by a metal tendon intermediate portion sliding over a metal tendon sliding surface and having a total winding angle of 90 degrees, that will result in the latter case to have a friction coefficient equal to substantially 0.5.

According to an embodiment, the encumber of said links 6, 7, 8 has a maximum extension, in a direction transversal to the longitudinal extension of said jointed subassembly 5 equal to or lower than 8 millimeters, and preferably equal to or lower than 5 millimeters, and preferably comprised in range from 2 millimeters to 5 millimeters.

According to an embodiment, said jointed subassembly 5 fits in its entirety in a cylindrical volume having a diameter measuring in range from 2 millimeters to 5 millimeters.

According to a preferred embodiment, said tendon 19, and preferably said tendon intermediate portion 28, has a diameter equal to or lower than 0.5 millimeters and preferably comprised between 0.005 millimeters and 0.5 millimeters.

According to an embodiment, said tendon has a substantially circular cross section. According to an embodiment, the diameter of said tendon is variable in different portions of said tendon. According to an embodiment, the mechanical properties of said tendon are variable in different portions of said tendon. According to an embodiment, said tendon is obtained by joining portions of tendons with different characteristics.

According to an embodiment, said control unit 4 is connected to an actuator drive unit 58, suitable for send said second command signal to said at least one actuator 25. According to an embodiment, said at least one control unit 4 comprises a CPU. According to an embodiment, said at least one control unit 4 comprises at least one processor unit. According to an embodiment, said at least one control unit 4 provides a feedback control circuit based on the information acquired by a detection system suitable for detecting the action, for example the displacement provided and/or the force exerted by, of said at least one actuator 25. According to an embodiment, said master tool 2 is designed to be handled by a surgeon 30. According to an embodiment, at least a portion of said surgical instrument 70 is designed to operate on the anatomy of a patient 29.

According to an embodiment, said surgical instrument 70 comprises at least one jointed subassembly 5.

According to an embodiment, the term "jointed subassembly" refers to a serial sequence of links connected one to the next by joints suitable to support and/or orient and/or position and/or influence the position of an end effector of said surgical instrument 70. According to an embodiment, from a functional point of view, said jointed subassembly can be a wrist joint, an elbow joint or a shoulder joint of a robotic or mechatronic structure.

According to an embodiment, said jointed subassembly 5 comprises links.

According to a preferred embodiment, said jointed subassembly 5 comprises at least a first link 6, a second link 7, and a third link 8. In this way, said jointed subassembly 5 comprises at least three links 6, 7, 8.

According to an embodiment, said first link 6 is formed of a first link structural body 9, said first link structural body 9 being in a single piece.

According to a preferred embodiment, the terminology "single piece" indicates that any degree of freedom is avoided within a single link structural body, when in operative conditions. According to an embodiment, the terminology "single piece" indicates that a link structural body can comprise two or more pieces joined together in such way to avoid any degree of freedom within a single link structural body.

According to an embodiment, the terminology "single piece" indicates also that a link structural body can comprise two or more pieces joined together in such way that the relative spatial orientation of said two or more pieces is rigidly locked, when in operative conditions.

According to an embodiment, the terminology "single piece" indicates also that a link structural body is monobloc.

According to an embodiment, said second link 7 is formed of a second link structural body 10, said second link structural body 10 being in a single piece.

According to an embodiment, said third link 8 is formed of a third link structural body 11, said third link structural body 11 being in a single piece.

According to an embodiment, each link is formed of a link structural body.

According to an embodiment, said first link structural body 9 comprises a first link distal portion 12 forming a first joint proximal portion, and said second link structural body 10 comprises a second link proximal portion 13 forming a first joint distal portion. According to an embodiment, said first link distal portion 12 of said first link structural body 9 comprises two clevis prongs, in such way to be suitable to form a clevis joint. According to an embodiment, said second link proximal portion 13 comprises two clevis prongs, in such way to be suitable to form a clevis joint.

According to an embodiment, said first link distal portion 12 and said second link proximal portion 13 cooperate to form at least partially a first joint 14 providing a single degree of freedom between said first link 6 and said second link 7. According to a preferred embodiment, said single degree of freedom between said first link 6 and said second link 7 is a roto-translational degree of freedom around a first joint axis X-X, and preferably, said roto-translational degree of freedom is a rotational degree of freedom around said first joint axis X-X.

According to an embodiment, said second link structural body 10 further comprises a second link distal portion 15 forming a second joint proximal portion, and said third link structural body 11 comprises a third link proximal portion 16 forming a second joint distal portion. According to an embodiment, said second link distal portion 15 comprises two clevis prongs, in such way to be suitable to form a clevis joint. According to an embodiment, said third link proximal portion 16 comprises two clevis prongs, in such way to be suitable to form a clevis joint.

According to an embodiment, said second link distal portion 15 and said third link proximal portion 16 cooperate to form at least partially a second joint 17 providing a single degree of freedom between said second link 7 and said third link 8. According to a preferred embodiment, said single degree of freedom between said second link 7 and said third link 8 is a roto-translational degree of freedom around a second joint axis Y-Y, and preferably said roto-translational degree of freedom is a rotational degree of freedom around said second joint axis Y-Y.

According to an embodiment, said first joint 14 and said second joint 17 are each suitable for providing a single degree of freedom.

According to an embodiment, said first joint 14 is suitable for locking the relative movement between said first link 6 and said second link 7 in all directions except for a relative rotation around a first joint axis X-X. According to an embodiment, said second joint 17 is suitable for locking the relative movement between said second link 7 and said third link 8 in all directions except for a relative rotation around a second joint axis Y-Y.

According to an embodiment, said first link structural body 9, said second link structural body 10 and said third link structural body 11 form a kinematic chain. According to an embodiment, said first link structural body 9, said second link structural body 10 and said third link structural body 11 are directly connected in series to form a kinematic chain According to an embodiment, said first link 6 is an adjacent link in respect of said second link 7, with no intervening links in the kinematic chain. According to an embodiment, said second link 7 is an adjacent link in respect of both said first link 6 and said third link 8. According to an embodiment, said third link 8 is an adjacent link in respect of said second link 7. According to an embodiment, said first link structural body 9 is an adjacent link structural body in respect of said second link structural body 10. According to an embodiment, said second link structural body 10 is an adjacent link structural body in respect of both said first link structural body 9 and said third link structural body 11. According to an embodiment, said third link structural body 11 is an adjacent link structural body in respect of said second link structural body 10.

According to an embodiment, said kinematic chain can comprises two or more branches of kinematic chain. According to an embodiment, said two or more branches extend from a single joint, for example from said second joint 17. According to an embodiment, said two or more branches of kinematic chain share at least one link. According to an embodiment, said two or more branches of kinematic chain share at least two links out of three links of the jointed subassembly.

According to an embodiment, each of said first joint 14 and said second joint 17 refer to mechanical means adapted to provide a link in the kinematic chain with a rotational degree of freedom around a joint axis with respect to an adjacent link in the kinematic chain. According to an embodiment, each of said joint axis X-X, Y-Y is a common joint axis shared by two adjacent links, such that the two adjacent links can rotate one with respect to the other around said common joint axis. According to an embodiment, said first joint 14 defines a first joint axis X-X, wherein said first joint axis X-X is a common joint axis shared by both said first link 6 and said second link 7, such that the two adjacent links can rotate one with respect to the other around said common joint axis. According to an embodiment, said second joint 17 defines a second joint axis Y-Y, wherein said second joint axis Y-Y is a common joint axis shared by both said second link 7 and said third link 8, such that the two adjacent links can rotate one with respect to the other around said common joint axis According to an embodiment, a kinematic chain formed by said at least three links 6, 7, 8 have two degrees of freedom.

According to an embodiment, a kinematic chain formed by said at least three links 6, 7, 8 have exactly two degrees of freedom. In other words, according to an embodiment, the total number of degrees of freedom of a kinematic chain formed by said at least three links 6, 7, 8 is two. According to an embodiment, a kinematic chain formed by said first link 6, said second link 7 and said third link 8 have exactly two degrees of freedom. In other words, according to an embodiment, the total number of degrees of freedom of a kinematic chain formed by said first link 6, said second link 7 and said third link 8 is two.

According to an embodiment, said jointed subassembly 5 avoids to comprise actuators. According to an embodiment, said jointed subassembly 5 avoids to comprise actuators within said kinematic chain. According to an embodiment, no actuators are provided among said links.

According to an embodiment, at least two among said first link structural body 9, said second link structural body 10 and said third link structural body 11 comprise at least one tendon sliding surface 66, avoiding that said at least one tendon sliding surface 66 is a hole surface. In other words, said at least one tendon contact surface 18 avoids to delimit a through hole in a link structural body 9 or 10 or 11. According to an embodiment, a normal line, or orthogonal line, to said at least one tendon sliding surface 66 avoids to intersect the structural body comprising said at least one tendon sliding surface 1866 According to an embodiment, said tendon sliding surface 66 avoids to face itself. According to an embodiment, said tendon contact surface 18 urges said tendon intermediate portion 28 away from the link structural body comprising said tendon sliding surface 66.

According to an embodiment, said tendon contact surface 18 embraces one of said tendon over an angle equal to or lower than 180 degrees. According to an embodiment, said tendon contact surface 18 is an outer surface of one of said link structural bodies 9, 10, 11. According to an embodiment, said tendon contact surface 18 delimits at least partially the encumber of one of said link structural bodies 9, 10, 11. According to an embodiment, each tendon comprises a first longitudinal side and a second opposite longitudinal side, wherein one between said first longitudinal side and said second longitudinal side is in contact with at least one of said links. In other words, when said first longitudinal side is in contact with a given link, said first longitudinal side faces away from said given link. According to an embodiment, each of said first longitudinal side and said second opposite longitudinal side covers on said tendon an angle of substantially 180 while remaining disjointed one another.

According to an embodiment, said surgical instrument 70 comprises tendons 19, 20, 21, 22, 23, 24, 31, 32. According to an embodiment, said tendons acts as actuation cables suitable for working only in traction.

According to an embodiment, said surgical instrument 70 comprises at least three tendons. Each tendon of said at least three tendons comprises a tendon proximal portion 26, associated to said at least one actuator 25, a tendon distal portion 27, secured to said second link 7 or to said third link 8, a tendon intermediate portion 28, extending between said tendon proximal portion 26 and said tendon distal portion 27.

According to an embodiment, said surgical instrument 70 comprises a further tendon so as to comprise at least four tendons, wherein said at least one intermediate portion 28 of each of said at least four tendons contacts said jointed subassembly 5 only in said at least one tendon sliding surface 66.

According to an embodiment, a pair of tendons have their tendon distal portions 27 secured to a same link, so as to work as. In other words, a pair of tendons are secured to a same link so as to work as antagonist tendons. According to an embodiment, a pair of tendons share their tendon distal portions 27, so as to work as antagonist tendons. According to an embodiment, a pair of tendons working as antagonist tendons are in single piece. According to an embodiment, said tendons 19, 20, 21, 22, 23, 24, 31, 32 comprises a first pair of tendons 19, 20, suitable to work as antagonist tendons. According to an embodiment, said tendons 19, 20, 21, 22, 23, 24, 31, 32 comprises a second pair of tendons 21, 22, suitable to work as antagonist tendons.

According to an embodiment, a pair of tendons have their tendon distal portions 27 secured to a same link, so as to work as one tendon. In other words, a pair of tendons are secured to a same link so as to work in parallel as a single tendon. According to an embodiment, a pair of tendons share their tendon distal portions 27, so as to work in parallel as a single tendon. According to an embodiment, a pair of tendons working as a single tendon are in single piece. According to an embodiment, said tendons 19, 20, 21, 22, 23, 24, 31, 32 comprises a first pair of tendons 19, 20, suitable to work as a single tendon. According to an embodiment, said tendons 19, 20, 21, 22, 23, 24, 31, 32 comprises a second pair of tendons 21, 22, suitable to work as a single tendon. According to an embodiment, said tendons 19, 20, 21, 22, 23, 24, 31, 32 comprises a third pair of tendons 23, 24, suitable to work as antagonist tendons. According to an embodiment, said tendons 19, 20, 21, 22, 23, 24, 31, 32 comprises a fourth pair of tendons 31, 32 suitable to work as antagonist tendons.

Figure 35:
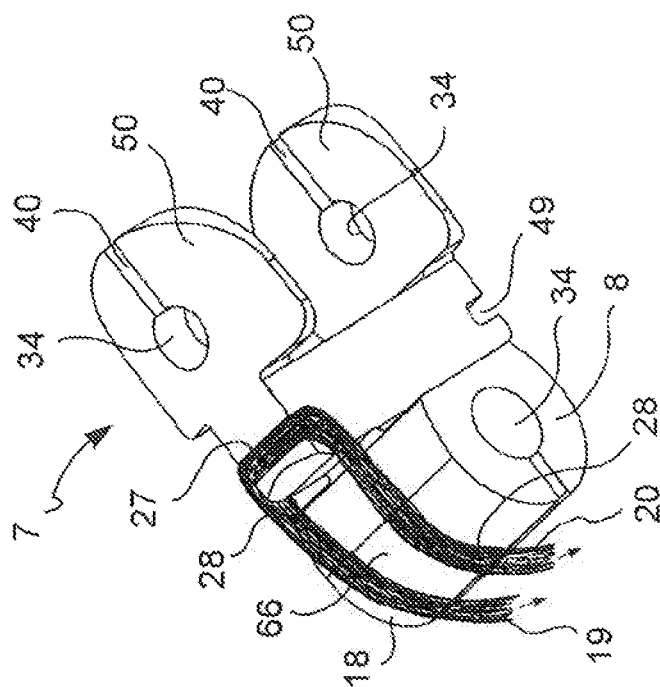
FIG. 35 is a perspective view of a link, according to an embodiment.
Figure 34:
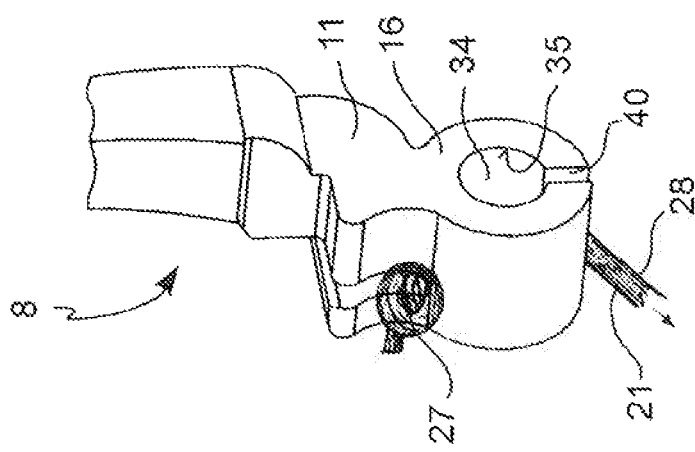
FIG. 34 is a perspective view of the link and the tendon shown in FIG. 33, depicted from the point of view indicated by the arrow XXXIV of FIG. 33.
Figure 33:
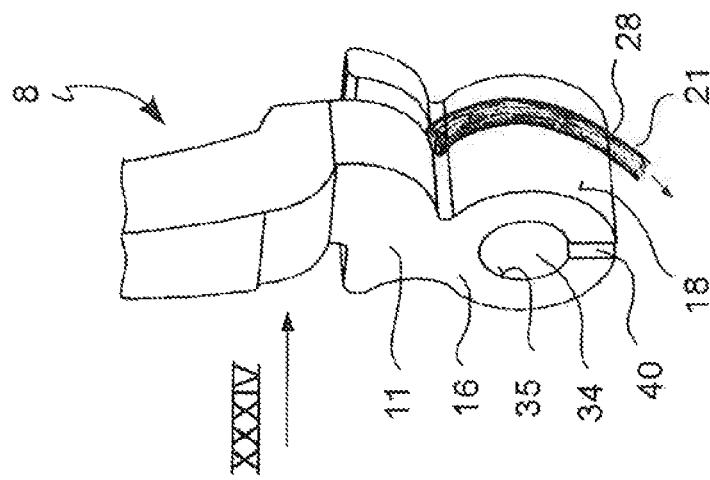
FIG. 33 is a perspective view of a link and a portion of a tendon, according to an embodiment.
Figure 36:
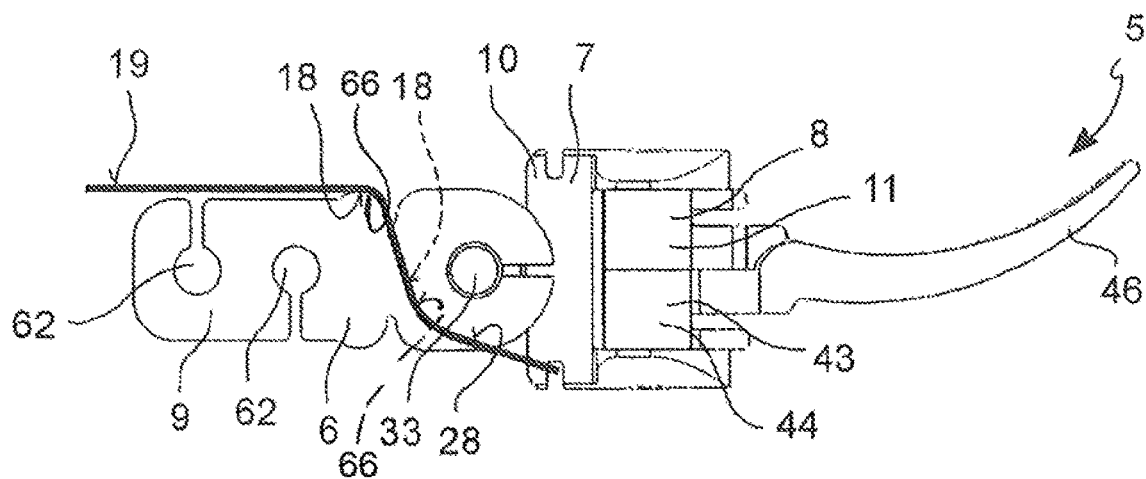
FIGS. 36 and 37 are plane views showing a jointed subassembly having transparent parts for sought of clarity and at least one tendon, according to some embodiments.
Figure 37:
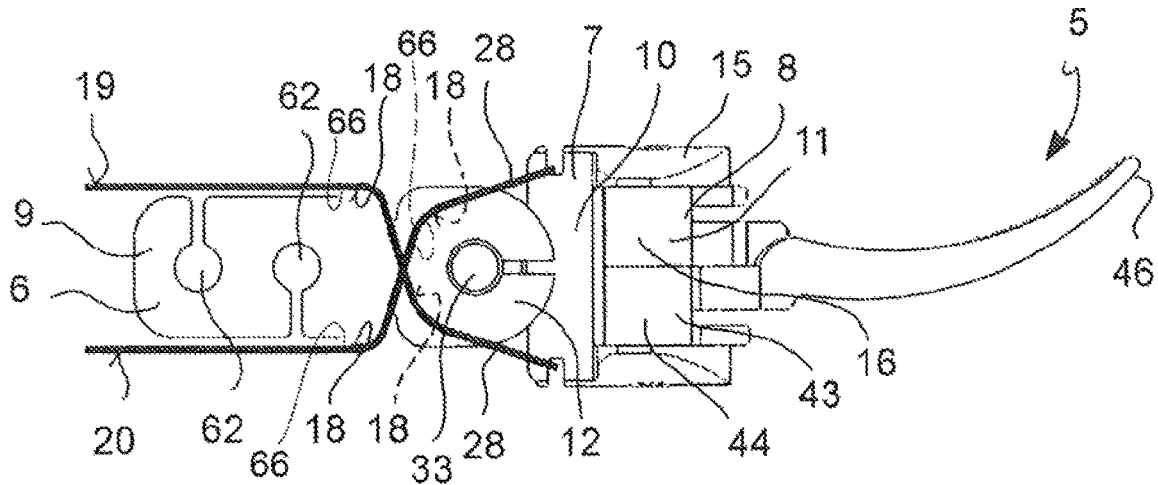
Figure 38:
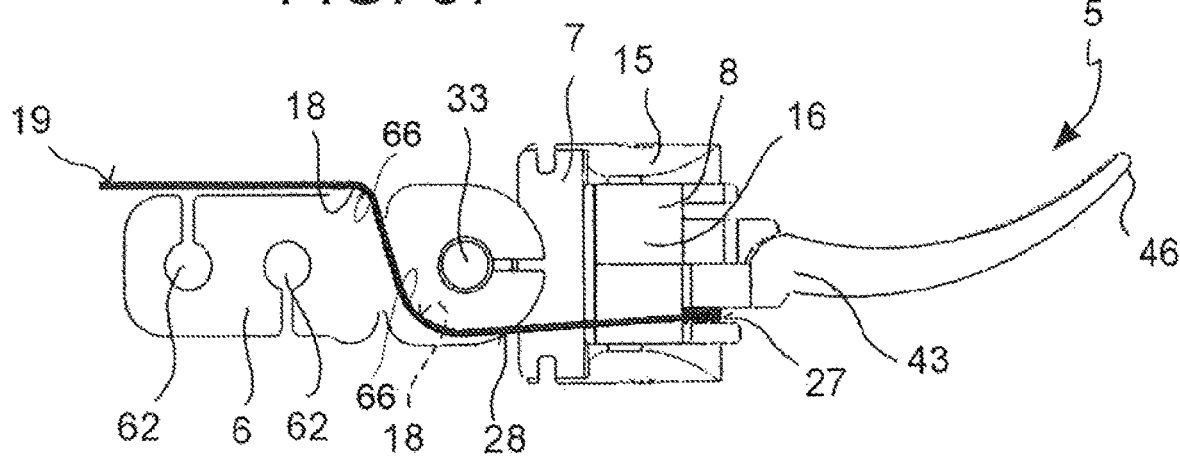
FIGS. 38 and 39 are plane views showing a jointed subassembly having transparent parts for sought of clarity and a tendon, according to some embodiments.
Figure 39:
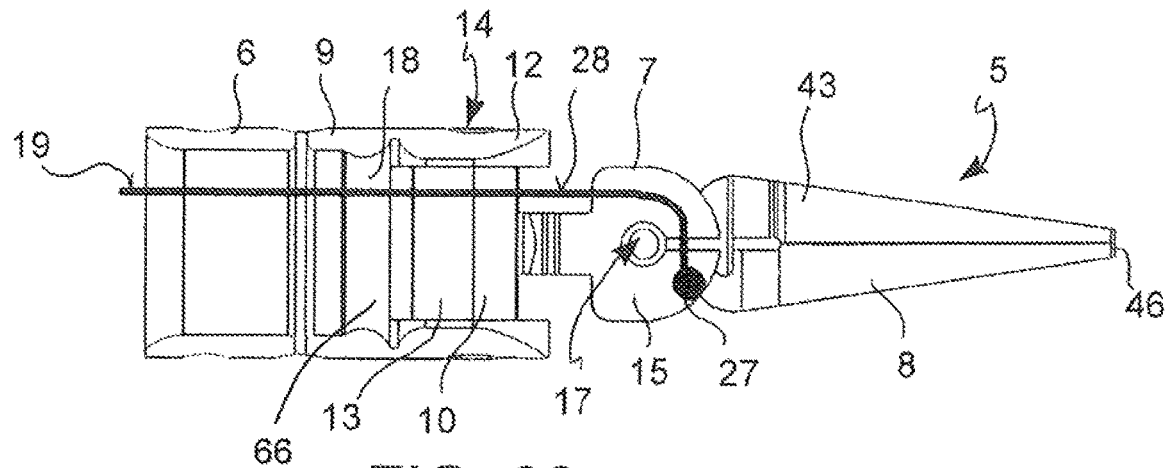
Figure 40:
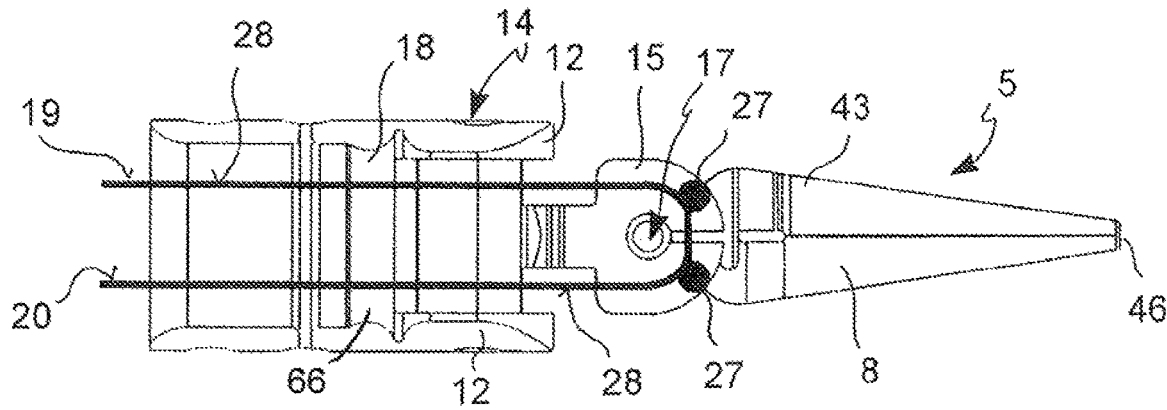
FIGS. 40 and 41 are plane views showing a jointed subassembly having transparent parts for sought of clarity and at least one tendon, according to some embodiments.
Figure 41:
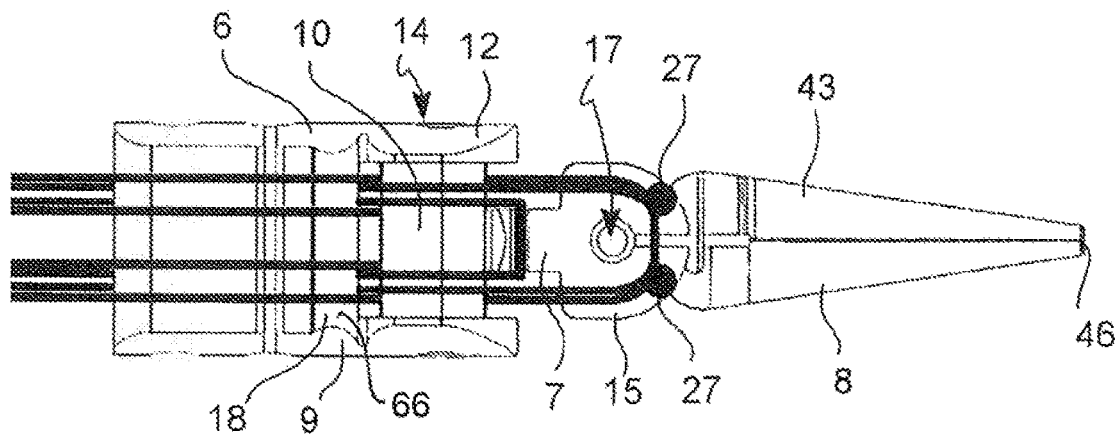
Figure 42:
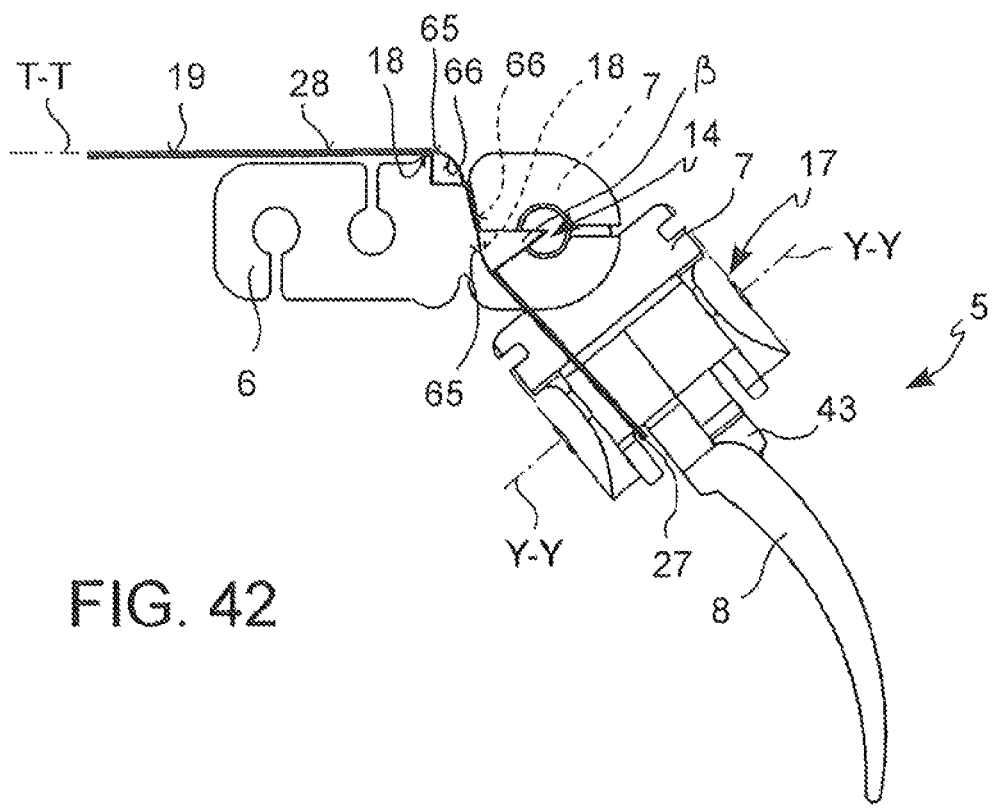
FIG. 42 is a sketch in plane view showing a configuration of a jointed subassembly, according to an embodiment, wherein a tendon describes a total winding angle.
Figure 43:
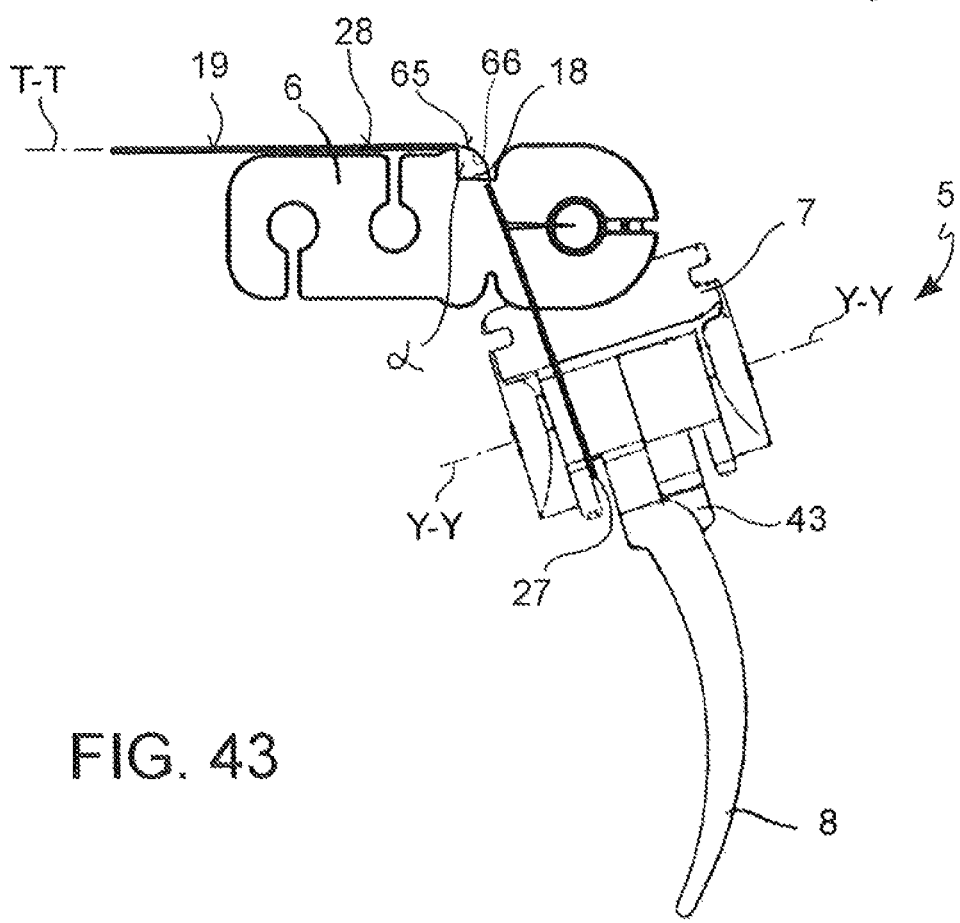
FIG. 43 is a sketch in plane view showing a configuration of a jointed subassembly, according to an embodiment, wherein a tendon describes a total winding angle.
Figure 44:
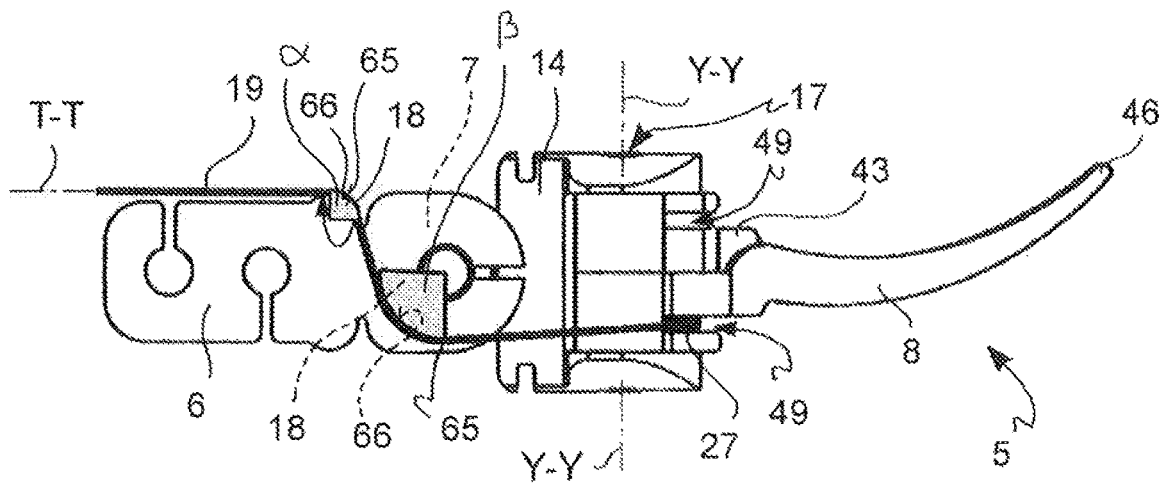
FIG. 44 is a sketch in plane view showing a configuration of a jointed subassembly, according to an embodiment, wherein a tendon describes a total winding angle.
Figure 45:
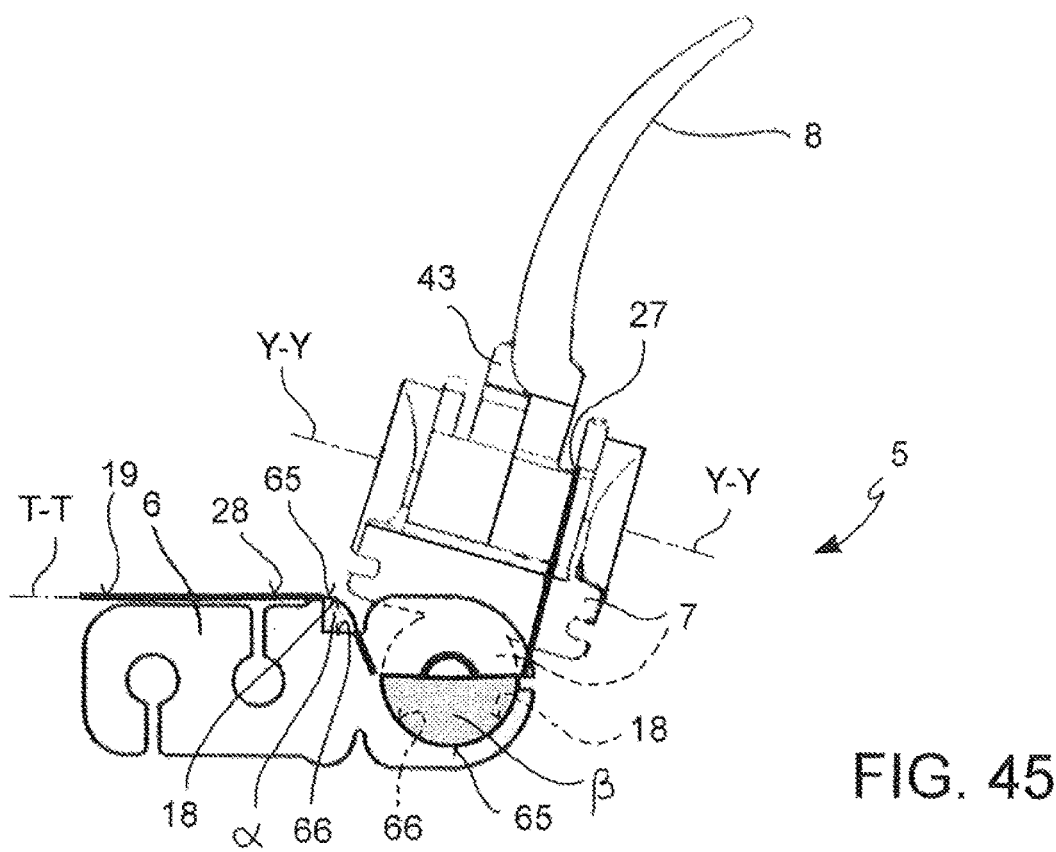
FIG. 45 is a sketch in plane view showing a configuration of a jointed subassembly, according to an embodiment, wherein a tendon describes a total winding angle.
Figure 46:
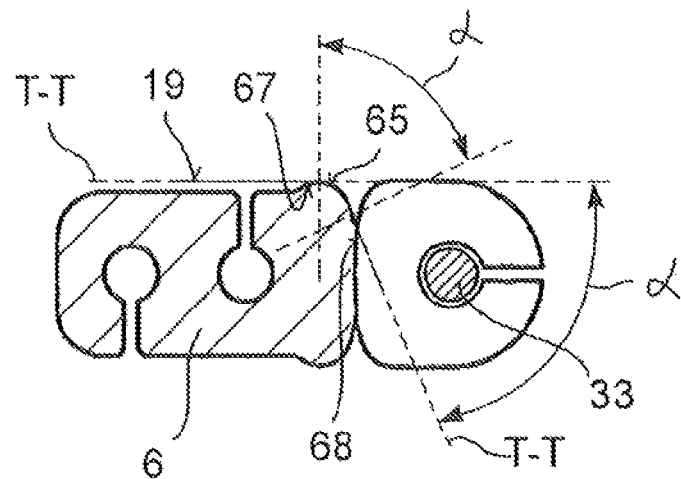
FIG. 46 is a sketch showing a cross-section of a link, according to an embodiment, wherein a tendon describes a local winding angle.
Figure 47:
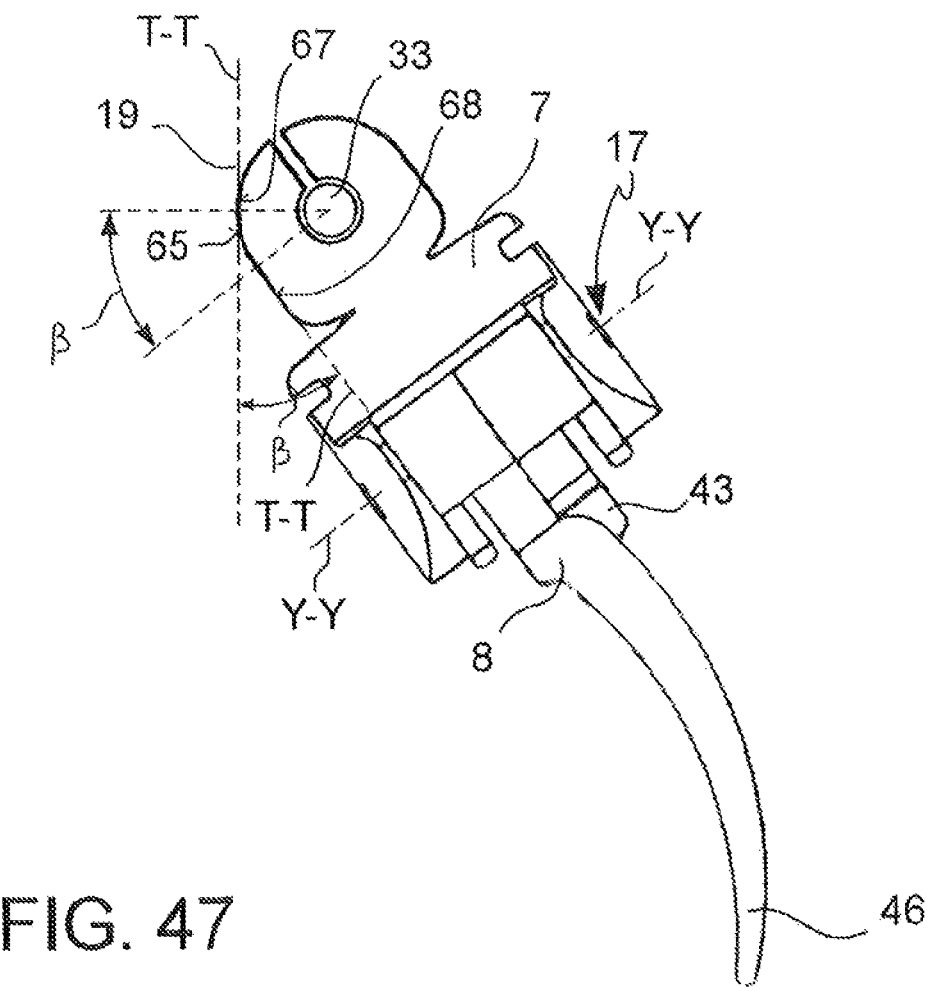
FIG. 47 is a sketch showing a cross-section of a link, according to an embodiment, wherein a tendon describes a local winding angle.

According to an embodiment, at least one between said second link 7 and to said third link 8 comprises at least a tendon securing portion 49, suitable to receive said tendon distal portion 27. According to an embodiment, at least one between said second link 7 and to said third link 8 comprises two tendon securing portions 49, suitable to receive said tendon distal portion 27 of two tendons working as antagonist tendons. For example, as shown in FIG. 35, said tendons 19 and 20 works in parallel as a single tendon.

According to an embodiment, said tendon intermediate portion 28 of each tendon contacts said jointed subassembly 5 exclusively in said at least one tendon sliding surface 66 of at least two among said first link structural body 9, said second link structural body 10 and said third link structural body 11. This avoids the need of any additional parts for routing the tendons and minimizes parts count and difficulty of assembly. This also avoids unnecessary friction and wear of tendons from further contact with the jointed assembly.

According to a preferred embodiment, this avoids that said tendon intermediate portion 28 of each tendon contacts any other portions of said jointed subassembly 5. According to an embodiment, said tendon intermediate portion 28 of each tendon contacts said jointed subassembly only in said at least one tendon sliding surface 66.

Advantageously, thanks to the characteristics of surgical instrument 70, it is possible to miniaturize the dimensions of said jointed subassembly 5.

According to an embodiment, each of said first link structural body 9, said second link structural body 10 and said third link structural body 11 comprise at least one tendon contact surface 18.

According to an embodiment, said at least one tendon sliding surface 66 is a groove surface. In other words, said tendon sliding surface, according to an embodiment, delimits at least partially a groove made in at least one link.

According to an embodiment, at least one link structural body of said link structural bodies can be associated to appendices in separate pieces with respect of said link structural body, such as pulleys, for example idle pulleys, i.e., pulleys rotatably connected to the link, but said appendices avoid to provide a contact surface for any one of said tendon intermediate portions 28.

According to an embodiment, said first link distal portion 12 and said second link proximal portion 13 cooperate in a geometric coupling, to form said first joint 14. According to an embodiment, said second link distal portion 15 and said a third link proximal portion 16 cooperate in a geometric coupling, to form said second joint 17.

According to an embodiment, at least one between said first joint 14 and said second joint 17 is a pivot joint. According to an embodiment, said pivot joint is a rotational joint which provides a mechanical pivot for the joint axis X-X or Y-Y.

According to an embodiment, at least one between said first joint 14 and said second joint 17 is a rolling joint. According to one embodiment, said rolling joint provides a rolling contact between a link structural body of a link and a link structural body of an adjacent link, over respective rolling surfaces such that the rolling motions happens around a fixed joint axis X-X or Y-Y.

According to an embodiment, at least one between said first joint 14 and said second joint 17 is a pin joint.

According to an embodiment, said pin joint comprises at least one pin 33 and at least one pin seat 34, suitable to receive said at least one pin 33. According to an embodiment, said pin 33 as a prevailing longitudinal development.

According to an embodiment, said at least one pin 33 is of smaller diameter that said at least one pin seat 34 receiving said at least one pin 33, so that a clearance results in the coupling of said pin 33 and said pin seat 34.

According to an embodiment, said pin seat 34 is a pass-through hole, delimited by at least one of said link structural bodies 9, 10, 11.

According to an embodiment, said pin seat 34 is a cavity, delimited by at least one of said link structural bodies 9, 10, 11.

According to an embodiment, said pin seat 34 is a cavity, having a cavity mouth 40 narrower than said at least one pin 33 and said cavity mouth 40 is unsuitable for receiving said pin 33. Such a cavity prevents the pin 33 from exiting the pin seat 34 in a direction transversal to the longitudinal development of said pin 33.

According to an embodiment, said pin seat 34 is delimited by a pin seat boundary 35 facing said pin seat 34. Preferably, said pin seat boundary 35 is suitable for facing a pin 33 received in said pin seat 34.

According to an embodiment at least one among said first link distal portion 12 of said first link structural body 9, said second link proximal portion 13 of said second link structural body 10, said second link distal portion 15 of said second link structural body 10, and said third link proximal portion 16 of said third link structural body 11, comprises said pin seat boundary 35 which delimits said pin seat 34 for receiving a pin 33.

According to an embodiment, said pin seat boundary 35 is substantially circular. According to an embodiment, said pin seat boundary 35 comprises an arch of a circumference. According to an embodiment, said pin seat boundary 35 describes a paraboloid profile. According to an embodiment, said pin seat boundary 35 describes a cam profile, suitable for cooperating with said pin 33 to form a cam-follower mechanism.

According to an embodiment, at least one between said first joint 14 and said second joint 17 is a cam joint.

According to an embodiment, at least one between said first joint 14 and said second joint 17 is a clevis joint. According to an embodiment, said clevis joint is formed by two clevis prongs 50 of a link structural body of a link which embraces a portion, and preferably a cylindrical mating portion, of a link structural body of an adjacent link.

According to an embodiment, said pin 33 is realized in separate piece in respect of said first link 6 and said second link 7 and associated to at least two pin seats 34, delimited by said first link distal portion 12 and said second link proximal portion 13, respectively, to form said first joint 14.

According to an embodiment, said pin 33 is realized in separate piece in respect of said second link 7 and said third link 8 and associated to at least two pin seats 34, delimited by said second link distal portion 15 and said third link proximal portion 16, respectively, to form said second joint 17.

According to an embodiment, said pin 33 is in single piece with a link 6 or 7 or 8.

According to an embodiment, said pin 33 is in single piece with a link structural body 9 or 10 or 11.

According to an embodiment, said at least one pin 33 is in single piece with said first link structural body 9 and projects cantilevered from said first link distal portion 12. According to an embodiment, said at least one pin 33 is in single piece with said second link structural body 10 and projects cantilevered from said second link proximal portion 13. According to an embodiment, said at least one pin 33 is in single piece with said second link structural body 10 and projects cantilevered from said second link distal portion 15. According to an embodiment, said at least one pin 33 is in single piece with said third link structural body 11 and projects cantilevered from said third link proximal portion 16.

Figure 19:
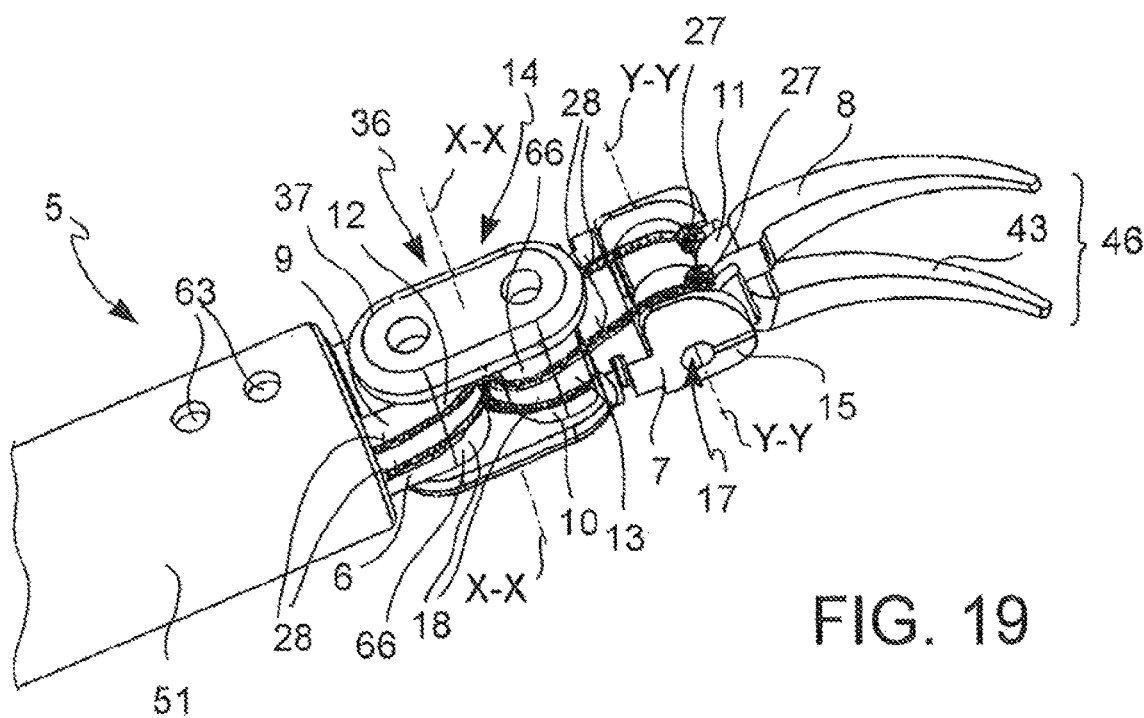
FIG. 19 is a perspective view of a jointed subassembly, according to an embodiment, wherein a double-jointed joint is shown.
Figure 20:
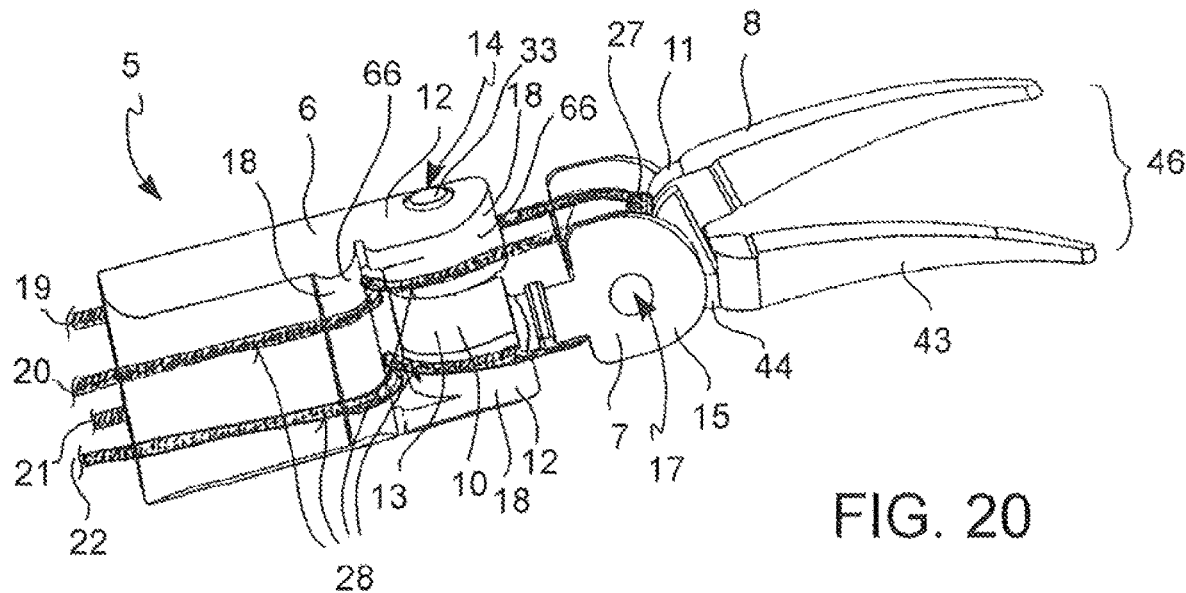
FIG. 20 is a perspective view of a jointed subassembly, according to an embodiment.
Figure 21:
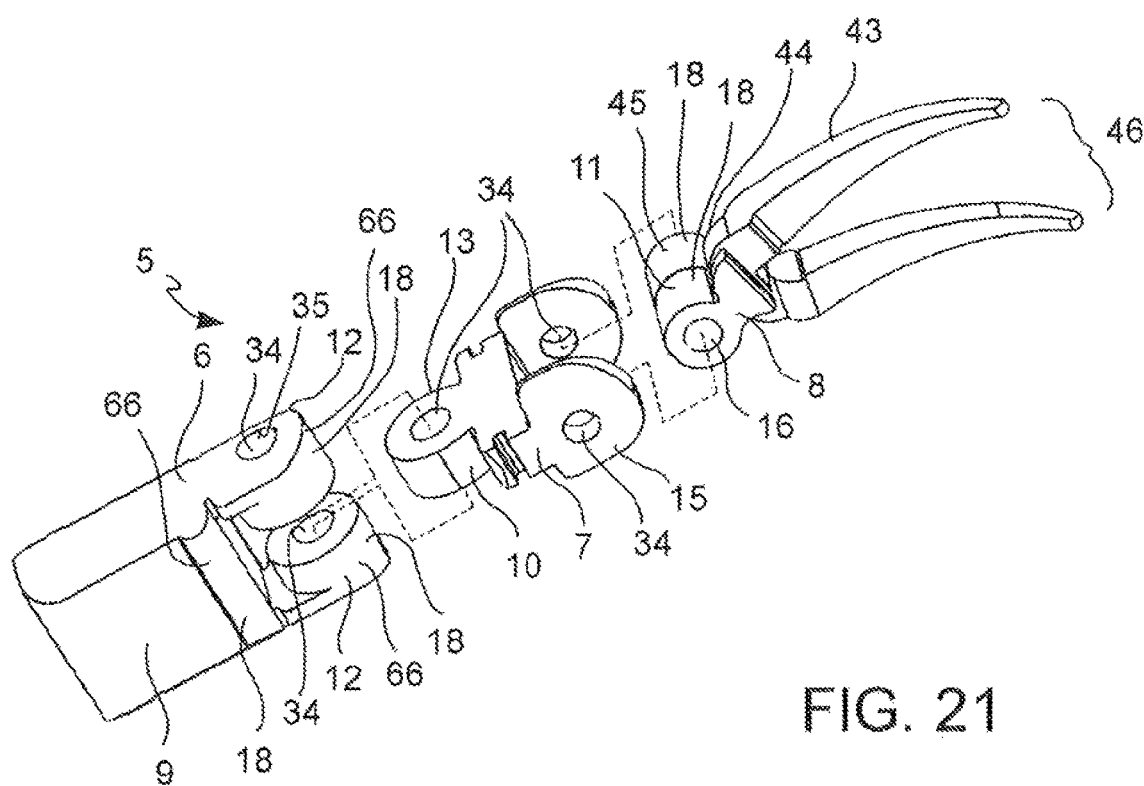
FIG. 21 is an exploded view of the jointed subassembly depicted in FIG. 20, wherein the tendons and the pins are not shown for sought of clarity.
Figure 23:
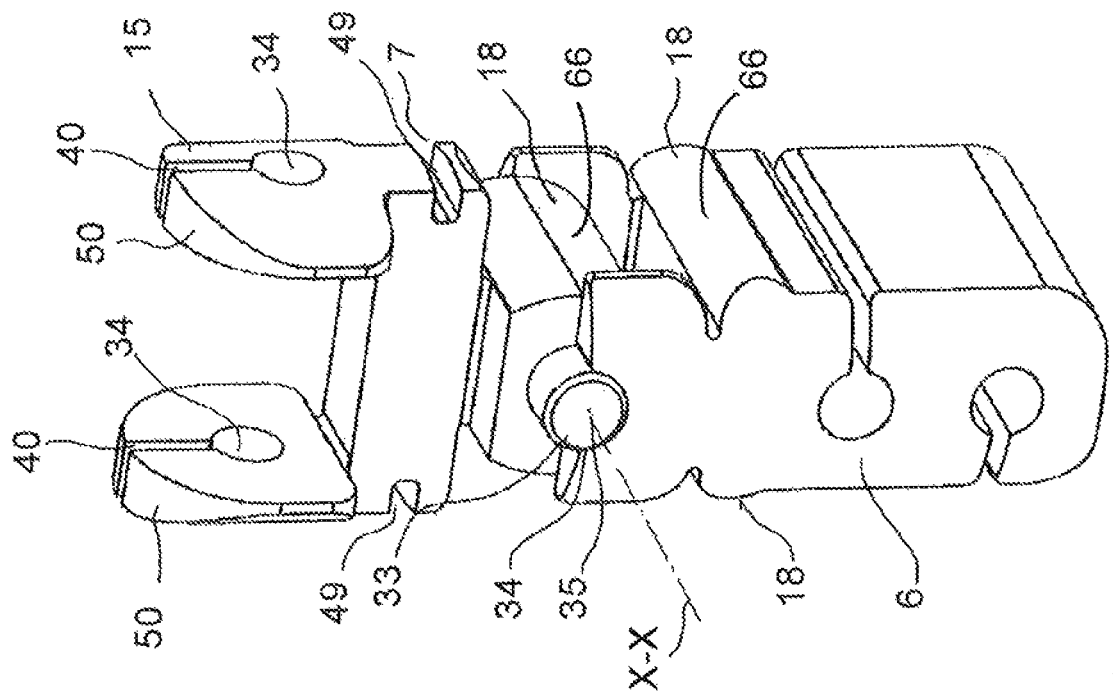
FIG. 23 is a perspective view of a joint of the jointed subassembly, according to an embodiment.
Figure 22:
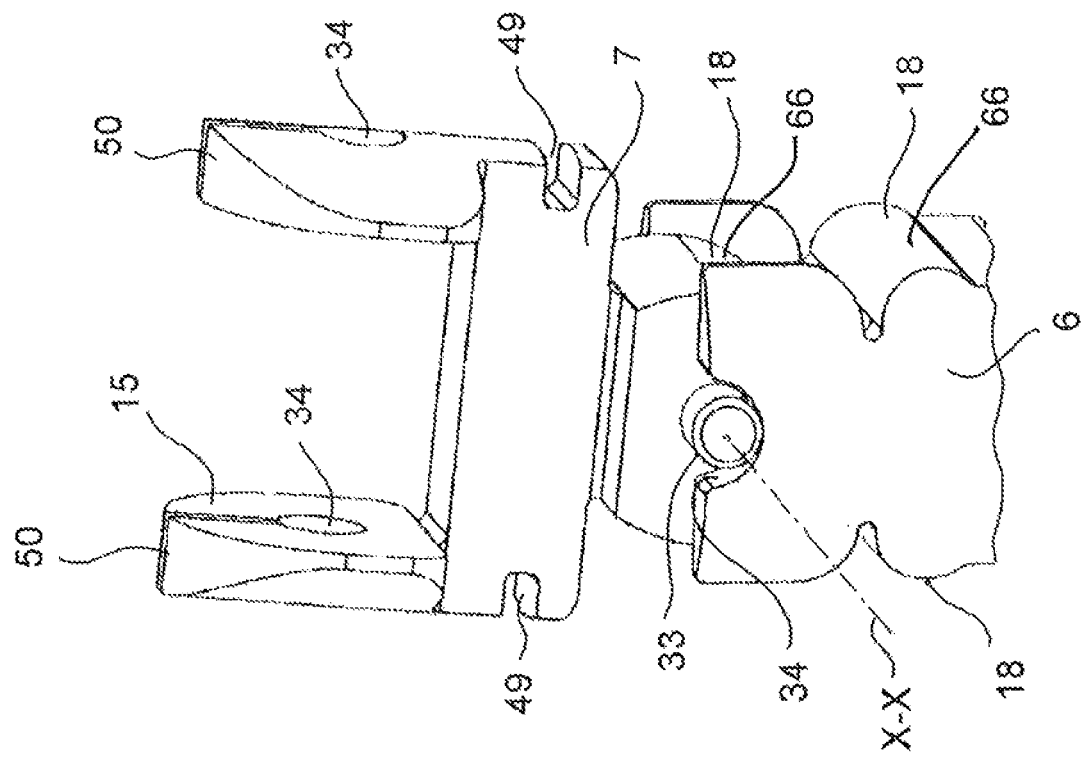
FIG. 22 is a perspective view of a joint of the jointed subassembly, according to an embodiment.

According to an embodiment, for example shown in FIG. 19, at least one between said first joint and said second joint is a double-joined joint 36. Thanks to such double-joined joint 36 is possible to provide a single degree of freedom between two adjacent links, ad detailed described in prior art document U.S. Pat. No. 5,710,870. According to an embodiment, said double-joined joint 36 comprises at least a hinge strut 37 connected to two of said link structural bodies. According to a preferred embodiment, said double-joined joint 36 comprises two opposite hinge struts 37.

According to one embodiment, said double-joined joint 36 is formed by a link and an adjacent link attached to each other via a pair of hinged struts 37. According to one embodiment, said link and said adjacent link pivot about first pivot axis and second pivot axis, wherein a constraining component constrains said link and said adjacent link to rotate with respect to each other. For example, said constraining component can be fixed spurs gears which mesh together or actuation cables routed appropriately. According to an embodiment, said constraining component is said at least one hinged strut 37.

Figure 24:
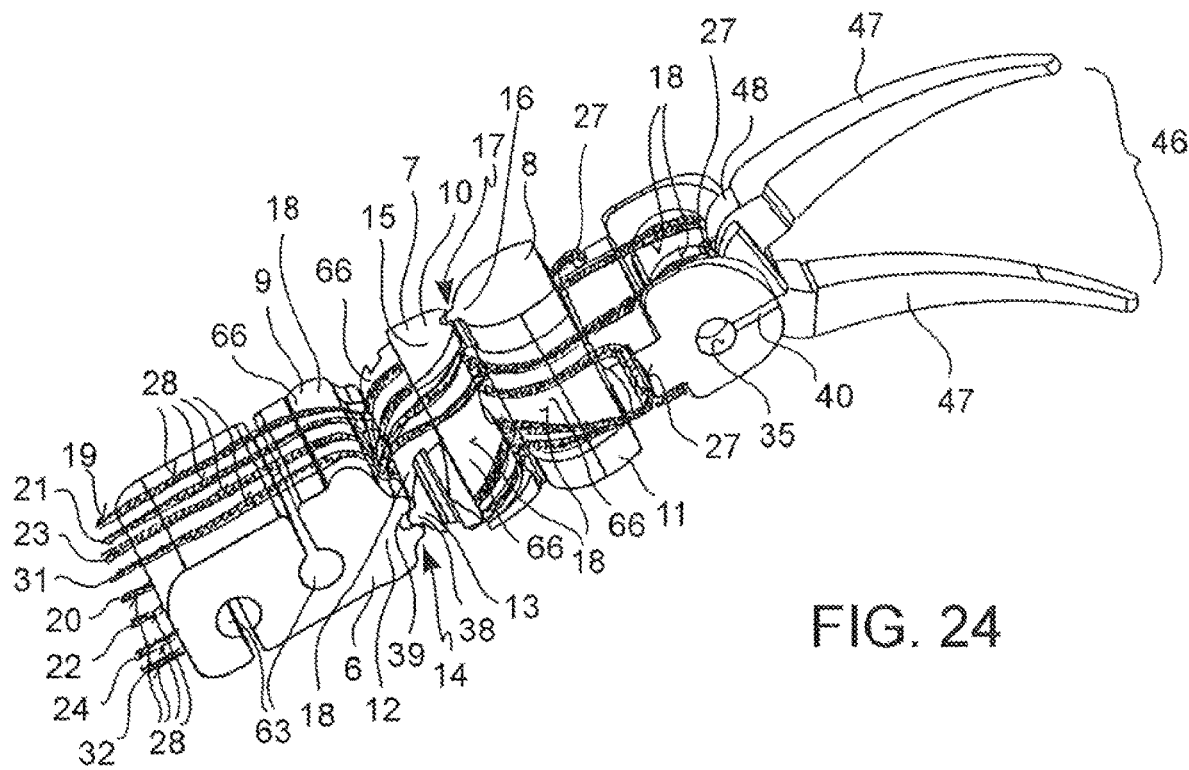
FIG. 24 is a perspective view of a jointed subassembly, according to an embodiment.
Figure 25:
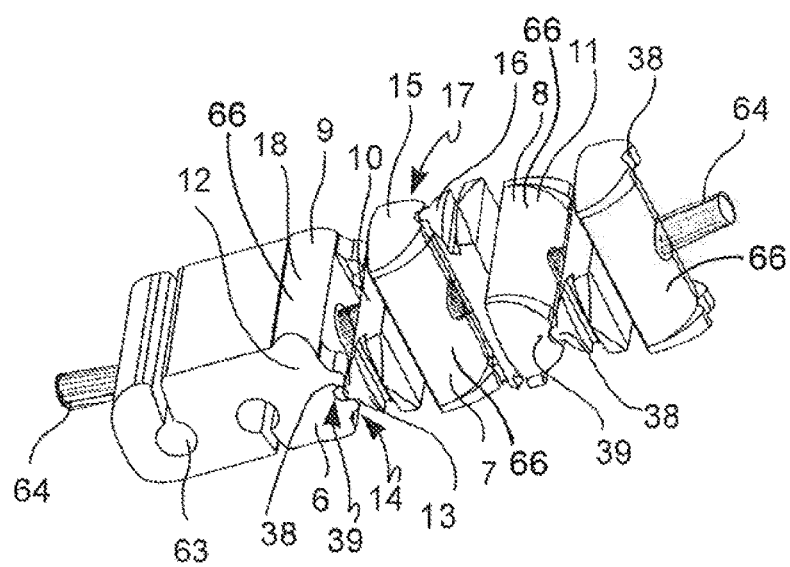
FIG. 25 is a perspective view of a portion of the jointed subassembly shown in FIG. 24, wherein the tendons are not shown for sought of clarity.
Figure 26:
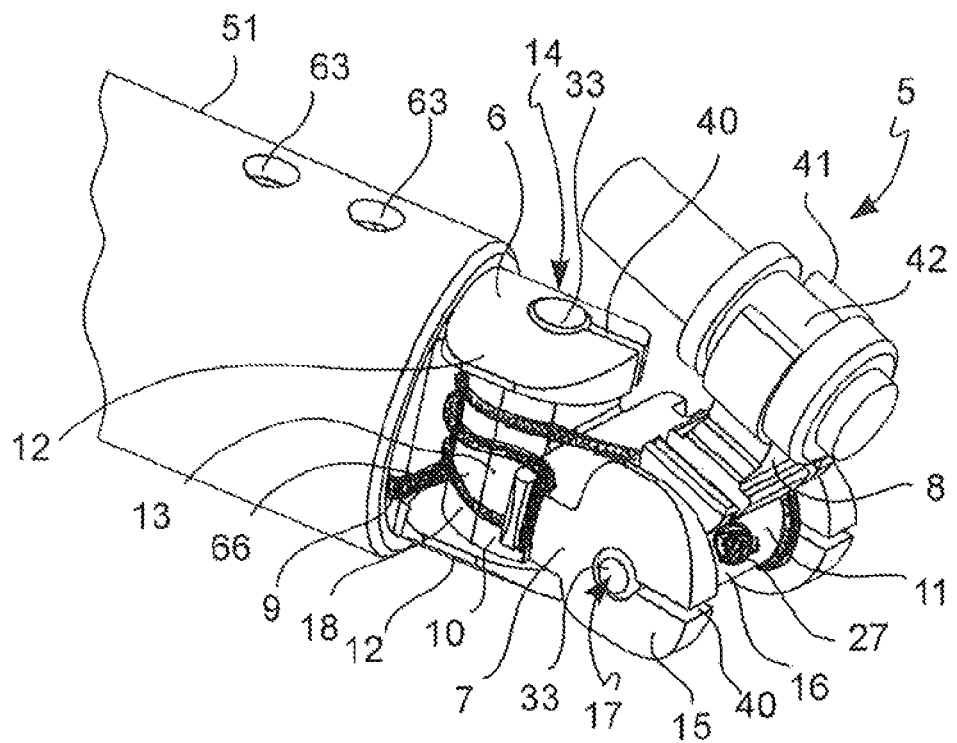
FIG. 26 is a perspective view of a jointed subassembly, according to an embodiment.
Figure 27:
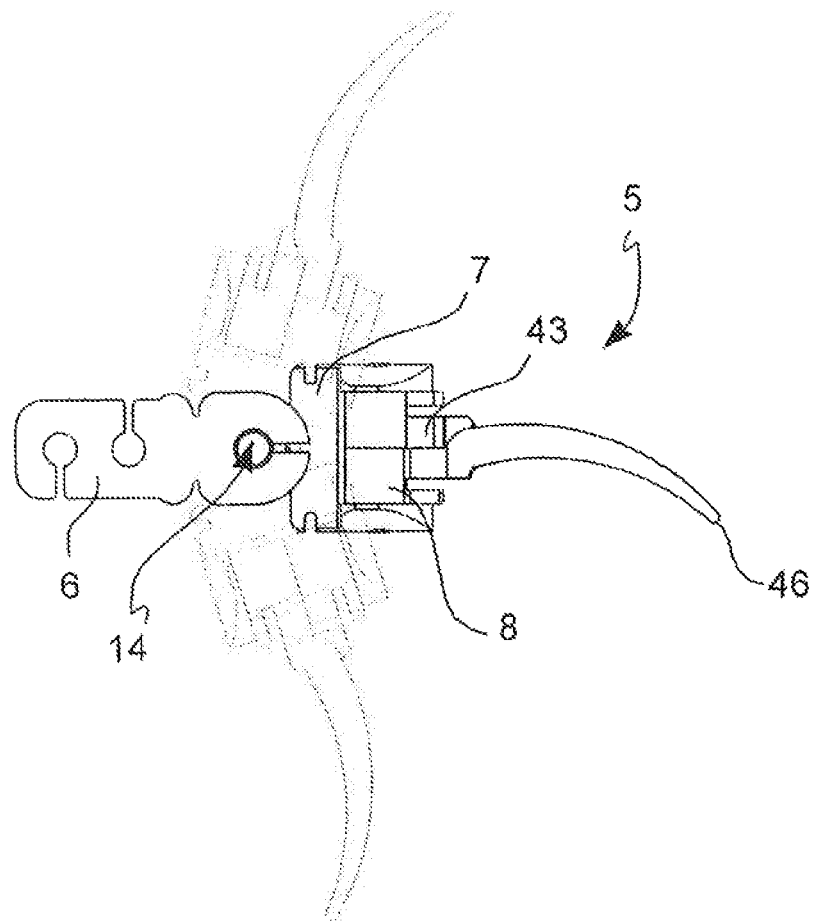
FIG. 27 is a plane views of a jointed subassembly showing three configurations of the jointed subassembly, according to an embodiment.
Figure 28:
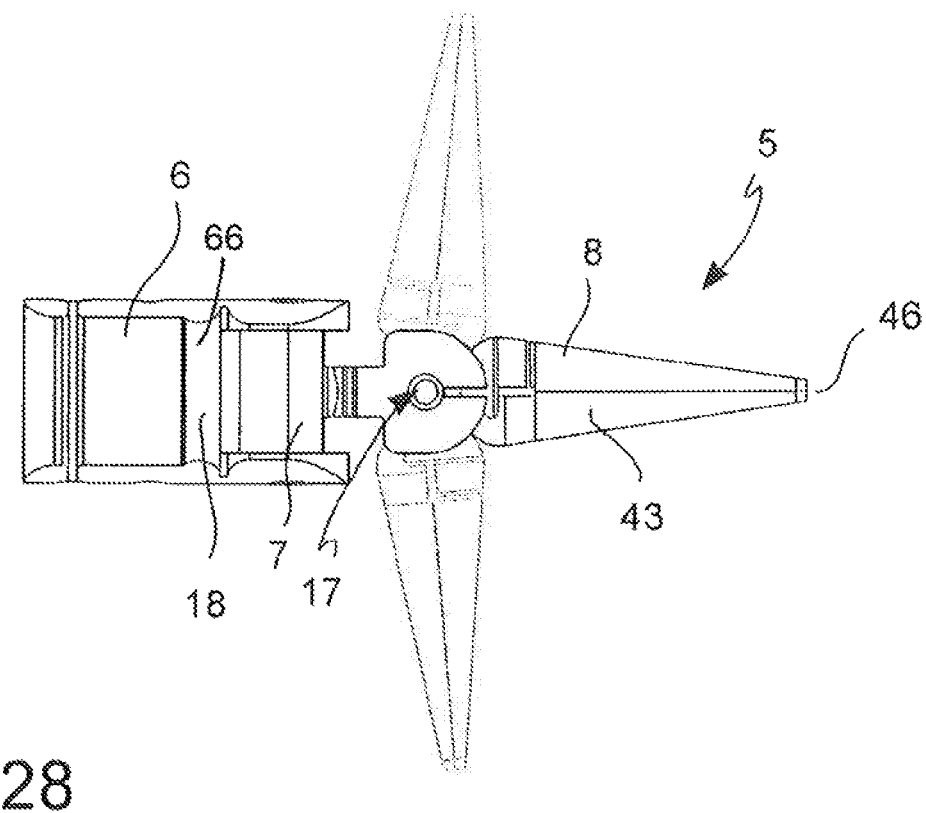
FIG. 28 is a plane views of a jointed subassembly showing three configurations of the jointed subassembly, according to an embodiment.
Figure 29:
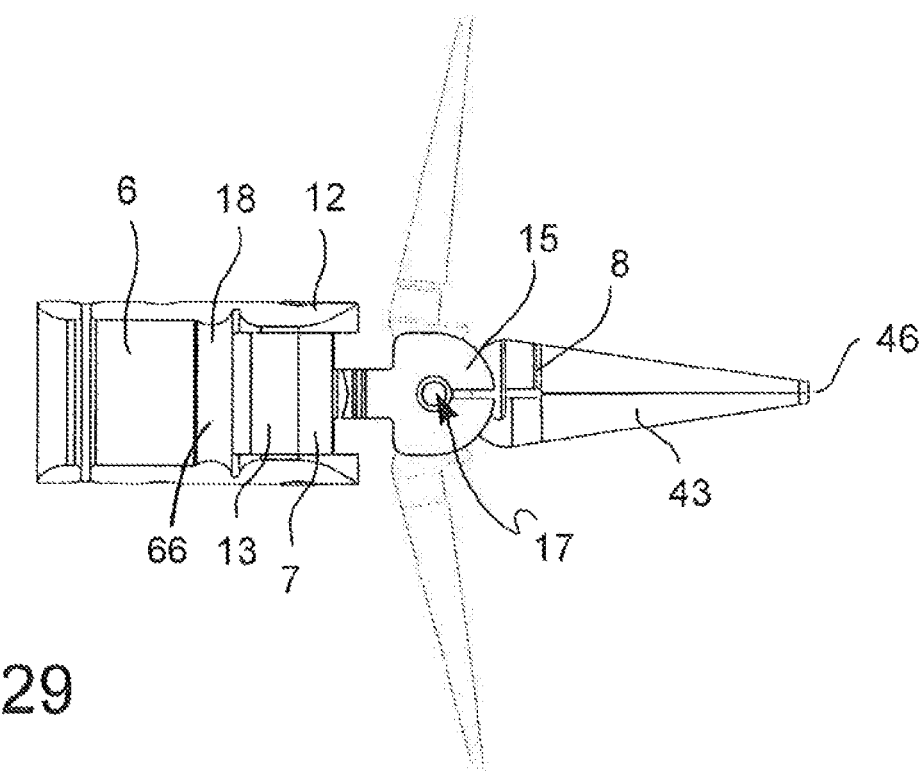
FIG. 29 is a plane views of a jointed subassembly showing three configurations of the jointed subassembly, according to an embodiment.
Figure 30:
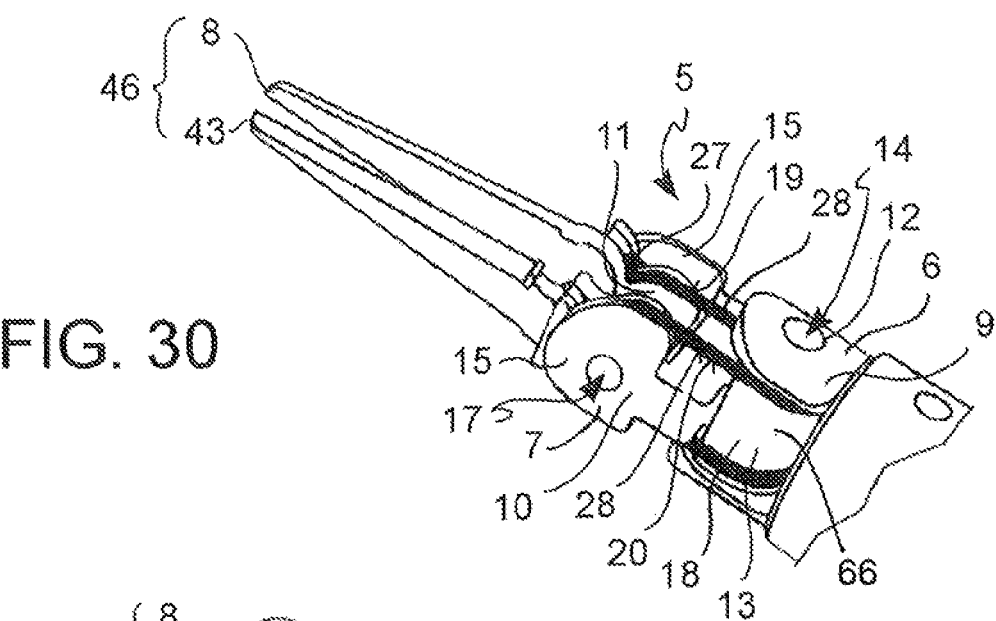
FIGS. 30, 31 and 32 are perspective views of a jointed subassembly, according to some embodiments.
Figure 31:
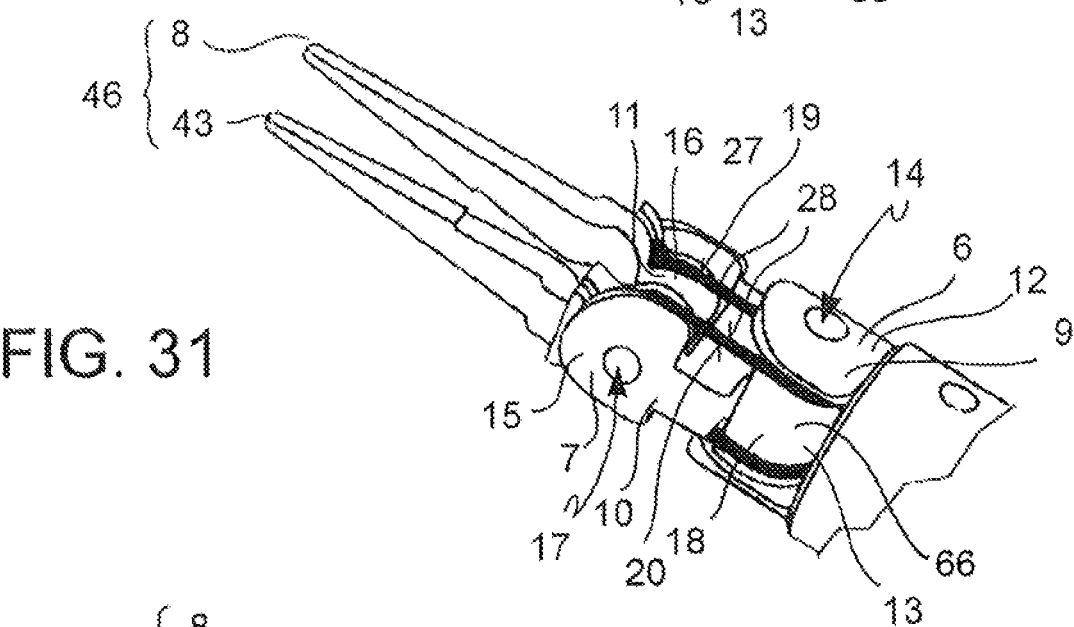
Figure 32:
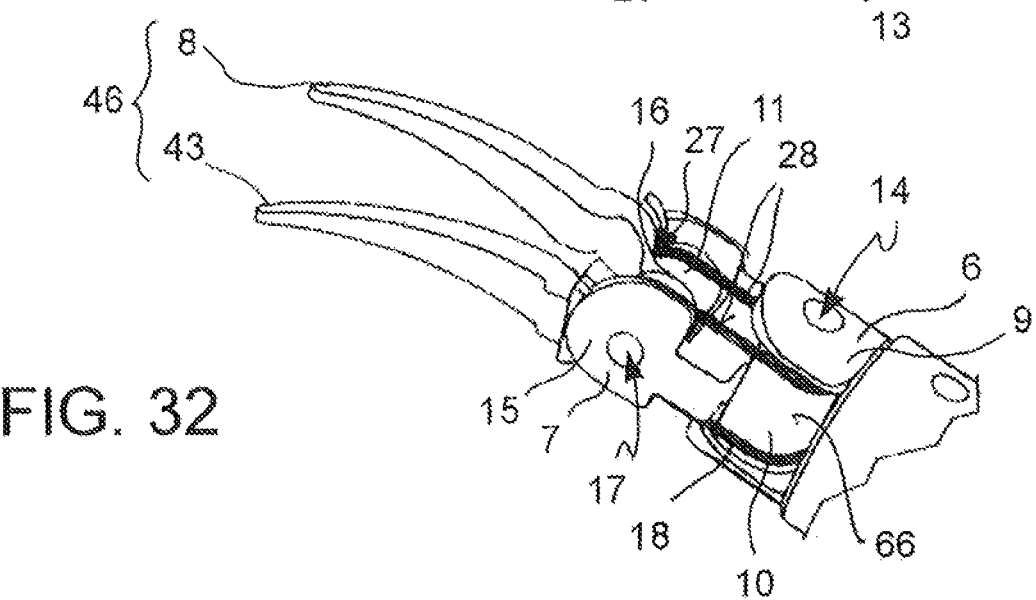

According to an embodiment, as shown for example in FIGS. 24 and 25, at least one between said first joint 14 and said second joint 17 is formed by opposite joint portions that intermesh one another. According to an embodiment, said first link distal portion 12 delimits at least a joint proximal groove 38 and said first link distal portion 13 comprises at least a joint distal tooth 39, said joint distal tooth 39 cooperates with said joint proximal groove 38 to form said first joint 14. According to an embodiment, said second link distal portion 15 delimits at least a joint proximal groove 38 and said second link distal portion 16 comprises at least a joint distal tooth 39, said joint distal tooth 39 cooperates with said joint proximal groove 38 to form said second joint 17. According to an embodiment, both said joint proximal groove 38 and said joint distal tooth 39 extends substantially parallel to a joint axis.

According to an embodiment, at least one of said links, preferably said third link 8, comprises a C-holder portion 41, suitable for receiving a terminal element 42. For example, said terminal element 42 can be a laser fiber, an irrigation tube, a suction tube or a tissue sensing probe.

According to an embodiment, said jointed subassembly 5 forms at least a portion of an end effector of said surgical instrument 70.

According to an embodiment, said jointed subassembly 5 is a wrist subassembly, wherein said first joint 14 is substantially orthogonal to said second joint 17. According to an embodiment, said jointed subassembly 5 is a wrist subassembly wherein said first joint axis X-X is substantially orthogonal to said second joint axis Y-Y.

According to an embodiment, said jointed subassembly 5 is an elbow subassembly, wherein said first joint 14 is substantially parallel to said second joint 17. According to an embodiment, said jointed subassembly 5 is an elbow subassembly, wherein said first joint axis X-X is substantially parallel to said second joint axis Y-Y.

According to an embodiment, said jointed subassembly 5 comprises a further third link 43 formed of a further third link structural body 44, said further third link structural body 44 being in a single piece.

According to an embodiment, said further third link structural body 44 of said further third link 43 comprises a further third link joint portion 45, said further third link joint portion 45 cooperates with said second link distal portion 15 of said second link structural body 10 of said second link 7 to form a portion of said second joint 17 providing a single degree of freedom between said second link 7 and said further third link 43. In this way, said second joint 17 provides a single degree of freedom between said second link 7 and said third link 8, a single degree of freedom between said second link and said further third link 43, and as a result a single degree of freedom between said third link 8 and said further third link 43.

According to an embodiment, said third link 8 forms a first branch of said kinematic chain and said further third link 43 forms a second a branch of said kinematic chain, wherein said first branch and said second branch are joined in said second joint 17. In this way said kinematic chain is a branched kinematic chain.

According to an embodiment, said third link 8 and said further third link 43 form an instrument tip 46 of said surgical instrument 70. According to an embodiment, said instrument tip 46 has an internal degree of freedom of grasp. According to an embodiment, said instrument tip 46 has at least one yaw degree of freedom in respect of said second link 7.

According to an embodiment, said jointed subassembly 5 comprises at least an additional link 47. According to an embodiment, said at least one additional link 47 is formed of an additional link structural body 48. According to an embodiment, said additional link structural body 48 is jointed to an adjacent link forming an additional joint. For example, said additional link structural body 48 can form an additional joint with a portion of said third link structural body 11. According to an embodiment, said additional link structural body 48 is jointed to an adjacent yet additional link structural body to form a joint.

According to an embodiment, said at least one tendon contact surface 18 is a ruled surface formed by a plurality of straight lines. According to an embodiment, each tendon contact surface 18 is a ruled surface formed by a plurality of straight lines. According to an embodiment, said plurality of straight lines are all parallel to a joint axis X-X or Y-Y. Preferably, said plurality of straight lines are all parallel to the joint axis X-X or Y-Y located closer to said at least one tendon contact surface 18.

According to an embodiment, said at least one tendon contact surface 18 is a convex surface.

According to an embodiment, at least one link structural body among said first structural body 9, said second structural body 10 and said third structural body 11 comprises more than one tendon contact surface 18.

According to an embodiment, all said more than one tendon contact surface 18 are convex surfaces defining with their prolongations thereof a single convex volume. According to an embodiment, the wording "convex volume" means that given a pair of points chosen inside said convex volume, the shorter straight conjunction between them is inside the convex volume in its entirety. This avoids providing grooves or channels on pulleys for guiding the tendons, allowing to further miniaturize the dimensions of the link structural bodies and of the jointed subassembly 5. According to an embodiment, all said more than one tendon contact surfaces 18 of said link structural body of at least one of said links define with their prolongations thereof a link convex hull of said link structural body. According to an embodiment, said link convex hull is defined as the volume comprised within a film wrapping one of said link.

According to an embodiment, said surgical instrument 70 comprises a shaft 51.

According to a preferred embodiment, said first link 6 is directly connected to said shaft 51.

According to an embodiment, said surgical instrument 70 comprises at least a frame 52, suitable for being detachably connected to a portion of said slave manipulator 3. According to an embodiment, said surgical instrument 70 comprises at least a frame 52, suitable for being detachably connected to an actuator compartment of said slave manipulator 3, said actuator compartment hosting said at least one actuator 25 defining a motor compartment 69 or motor box 69. According to an embodiment, said at least one actuator 25 is housed within a portion of said slave manipulator 3.

According to an embodiment, said surgical instrument 70 is detachably associated to said slave manipulator 3.

According to an embodiment, said surgical instrument 70 is associated in a reversible manner to said slave manipulator 3.

According to an embodiment, said shaft 51 extends between said frame 52 and said jointed assembly 5.

According to an embodiment, said shaft 51 is a rigid shaft. According to an embodiment, said shaft 51 has a hollow core that allows the passing of the tendons.

According to an embodiment, said shaft 51 is a flexible shaft. According to an embodiment, said shaft 51 comprises channels to guide at least one of said tendons.

According to an embodiment, said shaft 51 is proximally connected to said frame 52 and distally connected to said first link 6 of said jointed subassembly 5, forming a tubular element connection 61. According to an embodiment, said tubular element connection 61 is a rigid connection, avoiding to provide any degree of freedom between said shaft 51 and said first link 6. According to an embodiment, said tubular element connection 61 comprises at least two tubular element pins 62 inserted in tubular element pin seats 63, preferably holes. Preferably, said tubular element pin seats 63 are at least in number of two, for providing a rigid connection. According to an embodiment, said shaft is distally connected to said first link 6 and the connection includes a solder.

According to an embodiment, said shaft 51 defines a longitudinal shaft axis r-r, substantially coincident to the axis of longitudinal development of said shaft 51. According to an embodiment, said shaft 51 is suitable to rotate around said longitudinal shaft axis r-r to provide a roll motion to the jointed subassembly, in such way to provide said jointed subassembly 5 of a further degree of freedom of roll around said longitudinal shaft axis r-r.

According to an embodiment, said first link structural body 9, said second link structural body 10 and said third link structural body 11 each comprising a passing-through payload hole, and wherein all said passing-through payload holes are substantially aligned one another in such way to be suitable for receive a single payload element 64, preferably extending substantially along said kinematic chain. According to an embodiment, said payload element 64 is one of an irrigation tube, a laser fiber, a cautery wire, a pair of cautery wires, a bending sensing element, avoiding that said payload element 64 is a tendon and/or works as an actuation cable.

According to an embodiment, said tendon distal portion 27 comprises a boss. According to an embodiment, said tendon distal portion 27 comprises a loop. According to an embodiment, said tendon distal portion 27 comprises a knot. According to an embodiment, said tendon distal portion 27 comprises a portion which is glued to a portion of said jointed subassembly 5. According to an embodiment, said tendon distal portion 27 comprises a portion which is wrapped around a portion of a link 6, 7, 8 multiple times. According to an embodiment, said portion which is wrapped around with a curvature radius that is substantially equal to the diameter of the tendon.

According to an embodiment, said tendon proximal portion 26 is glued to a portion of said frame 52. According to an embodiment, said tendon is unraveled into strands around its first tendon proximal portion 26 such as to maximize the glued surface.

According to an embodiment, at least one of said tendons, and preferably each tendon of said tendons, is exclusively suitable to work under tensile load applied at the tendon proximal portion 26 and at the tendon distal portion 27, avoiding said tendon to be pinched, to be laterally guided in a channel or to comprise a sheath.

According to an embodiment, at least one of said tendons, and preferably each tendon of said tendons, is suitable to be pre-lengthened with a load cycle comprising at least two loads of an entity equal to at least half of the tensile breaking strength of said tendon.

According to an embodiment, said slave manipulator 3 comprises at least a micromanipulator, suitable for providing said surgical instrument 70 with three Cartesian degrees of freedom.

According to an embodiment, said at least one actuator 25 comprises at least a pushing element 53 and said surgical instrument 70 comprises, in its proximal frame 52, at least a plunger 54 associated to a tendon, wherein, whenever said surgical instrument 70 is connected with said slave manipulator 3, said pushing element 53 is suitable for pushing against said plunger 54 to determine that the plunger 54 deflects the tendon proximal portion 26 of the tendon associated thereto and to obtain a movement of a link associated to the tendon distal portion of said tendon.

According to an embodiment, a sterile barrier 55 is interposed between said slave manipulator 3 and said surgical instrument 70. According to an embodiment, a sterile barrier 55 is interposed between said at least one pushing element 53 of said slave manipulator 3 and said at least one plunger 54 of said surgical instrument 70. According to an embodiment, said at least one plunger is associated to an elastic element 56 suitable for biasing the plunger against said tendon proximal portion 26 associated thereto. According to an embodiment, said plunger 54 comprises a tendon contact portion 57 which contacts said tendon proximal portion 26. According to an embodiment, said tendon contact portion 57 of said plunger 54 comprises a guide pulley. According to an embodiment, said tendon proximal portion 26 is guided by a plurality of pulleys.

According to a general embodiment, it is provided a surgical instrument 70 according to any one of the embodiments previously described.

According to a general embodiment, it is provided a slave assembly comprising at least a slave manipulator 3 according to any one of the embodiments previously described and at least a surgical instrument 70 according to any one of the embodiments previously described.

By virtue of the features described above, provided either separately or in combination, where applicable, in particular embodiments, it is possible to satisfy the sometimes contrasting needs disclosed above, and to obtain the aforesaid advantages, and in particular:

- it is provided a miniaturization of slave surgical instrument;
- an extreme miniaturization below 5 mm of transversal diameter of the jointed subassembly can be achieved, without employing idle pulleys, and without employing hole or guide channels that pass through any of the structural bodies of the three links;
- it is achieved that the tendons that slide over the structural body of an intermediate link to actuate a more distal link and wrap around the intermediate link structural body by 90 degrees already when the jointed subassembly, for example a wrist subassembly, is in its straight configuration, and while this is taught against by prior art due to the increase of sliding friction that it produces, in some embodiments disclosed above, the 90 degrees wrap allows to slide the tendons on the outer surfaces of the links, rather than passing them through holes or channels, in order to constrain the tendons to stay within the diameter of the link when the distal links are bent;
- the tendons can lay in equilibrium on said outer surfaces of the links, finding their minimum energy path resulting from their tension and the surface friction forces, avoiding altogether sharp bends, and in this way, it is enabled the use of polymeric tendons, such a polyethylene, UHMWPE that are known to be stronger than steel and with much lower friction over metallic substrate, such as steel, for the tendon material or outer material, as said polymeric tendons made in polyethylene or UHMWPE, unlike steel tendons or other polymeric tendons, suffer abrasion caused by sliding over sharp edges or side walls, and therefore a design that routes the tendons over the outer surfaces of the links laying them in equilibrium on said outer surfaces allows the polymeric tendon to flatten on said outer surface and minimize its abrasion;
- the total friction between the tendon and the links can be greatly reduced rather than increased, because the increase in larger winding angle or wrap angle in the capstan equation (by 90 degrees, equal to approx. 1.5 radians) is effectively countered by a reduction of the friction coefficient from 0.5 of steel cables over steel to 0.04 to 0.08 for polyethylene over steel alloys.

Those skilled in art may make many changes and adaptations to the embodiments described above or may replace elements with others which are functionally equivalent in order to satisfy contingent needs without however departing from the scope of the appended claims.

LIST OF REFERENCES

1 Robotic microsurgery assembly
2 Master tool
3 Slave or slave manipulator
4 Control unit
5 Jointed subassembly
6 First link
7 Second link
8 Third link
9 First link structural body or structural body of said first link
10 Second link structural body or structural body of said second link
11 Third link structural body or structural body of said
12 First link distal portion of said first link structural body
13 Second link proximal portion of said second link structural body
14 First joint
15 Second link distal portion of said second link structural body
16 Third link proximal portion of said third link structural body
17 Second joint
18 Tendon contact surface
19, 20, 21, 22, 23, 24, 30, 31 Tendons
25 Actuator
26 Tendon proximal portion
27 Tendon distal portion
28 Tendon intermediate portion
29 Patient
30 Surgeon
33 Pin
34 Pin seat
35 Pin seat boundary
36 Double-joined joint
37 Hinge strut
38 Joint proximal groove
39 Joint distal tooth
40 Cavity mouth
41 c-holder portion
42 Terminal element
43 Further third link
44 Further third link structural body
45 Further third link joint portion
46 Instrument tip
47 Additional link
48 Additional link structural body
49 Tendon securing portion
50 Clevis prong
51 Shaft
52 Frame
53 Pushing element
54 Plunger
55 Sterile barrier
56 Elastic element
57 Tendon contact portion of the plunger
58 Actuator drive unit
59 First command signal
60 Second command signal
61 Tubular element connection
62 Tubular element pin
63 Tubular element pin seat
64 Payload element
65 Sliding path
66 Tendon sliding surface
67 Proximal contact surface border
68 Distal contacxt surface border
69 Motor box or motor compartment
70 Medical Instrument or Surgical Instrument or Instrument
X-X First joint axis
Y-Y Second joint axis
r-r Longitudinal direction of the shaft
T-T Tendon longitudinal path
$\alpha$ Local winding angle or first local winding angle
ß Local winding angle or second local winding angle
$\alpha$+ß Total winding angle

The invention claimed is:

1. A surgical instrument comprises a jointed subassembly comprising:
a first link and a second link associated in a joint providing a degree of freedom between said first link and said second link;
a third link moveable with respect to said second link; and
a tendon secured to said third link to actuate said third link;
wherein
said first link comprises at least one tendon contact surface on which said tendon slides, defining one or more curved sliding paths, and
said second link comprises at least one tendon contact surface on which said tendon slides, defining one or more curved sliding paths;
each of said sliding paths subtends a local winding angle, wherein a sum of all local winding angles defines a total winding angle, and wherein said total winding angle is between 60 degrees and 300 degrees.

2. The surgical instrument of claim 1, wherein the total winding angle is between 90 degrees and 270 degrees.

3. The surgical instrument of claim 1, wherein the total winding angle is equal to or greater than 120 degrees in at least one configuration of said jointed subassembly.

4. The surgical instrument of claim 1, wherein the total winding angle is equal to or greater than 90 degrees when said jointed subassembly is in an unfolded configuration.

5. The surgical instrument of claim 1, wherein the contact surfaces are convex surfaces.

6. The surgical instrument of claim 1, wherein the contact surfaces are cylindrical surfaces.

7. The surgical instrument of claim 1, wherein the contact surface is a ruled surface with parallel straight generator lines.

8. The surgical instrument of claim 1, wherein each link is in single piece.

9. The surgical instrument of claim 1, wherein said third link is connected to the second link forming a second joint.

10. The surgical instrument of claim 1, wherein said third link is part of a tip of the surgical instrument.

11. The surgical instrument of claim 1, wherein said tendon is a polymeric tendon.

12. The surgical instrument of claim 1, wherein the mechanical properties of the tendon are variable along a length of the tendon.

13. The surgical instrument of claim 1, wherein one link between said first link and said second link comprises at least two tendon contact surfaces on which said tendon slides remaining in contact with both of said at least two tendon sliding surface, thereby defining a sliding path on each of said at least two tendon contact surfaces of said one link between said first link and said second link.

14. The surgical instrument of claim 1, wherein said third link further comprises at least a tendon contact surface which is incompatible for said tendon to slide thereon, thereby avoiding defining a sliding path.

15. The surgical instrument of claim 1, wherein each sliding path is a continuous path with a prevailing longitudinal extension as a result of an imprint that the sliding tendon defines on said tendon contact surfaces of the first link and of the second link.

16. The surgical instrument of claim 1, wherein said tendon slides along a longitudinal development avoiding sliding in a direction transversal to the tendon longitudinal development.

17. A robotic surgical assembly comprising at least one surgical instrument according to claim 1, and
a slave manipulator comprising at least one actuator;
wherein said at least one surgical instrument is connectable to said slave manipulator.

18. The robotic surgical assembly of claim 17, wherein said tendon comprises:
a tendon proximal portion operatively coupled to said at least an actuator of the slave manipulator;
a tendon distal portion secured to said third link; and
a tendon intermediate portion extending between said tendon proximal portion and said tendon distal portion;
wherein said tendon intermediate portion slides defining said one or more sliding paths on said first link and said second link.

19. The robotic surgical assembly of claim 18, wherein said tendon distal portion is incompatible for sliding on a tendon contact surface.

20. The surgical instrument of claim 1, wherein each contact surface is a portion of a cylindrical surface.

\* \* \* \* \*